United States Patent
Pratt et al.

(10) Patent No.: US 8,317,998 B2
(45) Date of Patent: Nov. 27, 2012

(54) METHODS OF OPERATION OF ELECTROCHEMICAL GAS SENSORS

(75) Inventors: Keith Francis Edwin Pratt, Portsmouth (GB); John Chapples, Portsmouth (GB); Martin Jones, Havant (GB); Stefan Dan Costea, Bucharest (RO); Mihai Gologanu, Bucharest (RO)

(73) Assignee: Life Safety Distribution AG, Uster (CH)

( * ) Notice: Subject to any disclaimer, the term of this patent is extended or adjusted under 35 U.S.C. 154(b) by 297 days.

(21) Appl. No.: 12/754,023

(22) Filed: Apr. 5, 2010

(65) Prior Publication Data
US 2010/0252455 A1    Oct. 7, 2010

(30) Foreign Application Priority Data
Apr. 6, 2009 (EP) .................... 09157370

(51) Int. Cl.
G01F 1/64 (2006.01)
G01N 17/00 (2006.01)
G01N 27/26 (2006.01)

(52) U.S. Cl. .......... 205/784; 204/431; 204/432; 73/1.06
(58) Field of Classification Search .......... 205/792; 204/431, 432; 73/1.06
See application file for complete search history.

(56) References Cited

U.S. PATENT DOCUMENTS

| | | | |
|---|---|---|---|
| 4,132,616 A | 1/1979 | Tantram et al. | |
| 5,558,752 A | 9/1996 | Wang et al. | |
| 5,611,909 A | 3/1997 | Studer | |
| 5,733,436 A * | 3/1998 | Demisch et al. | 205/775 |
| 5,741,413 A | 4/1998 | Capetanopoulos | |
| 6,165,347 A | 12/2000 | Warburton | |
| 6,428,684 B1 | 8/2002 | Warburton | |
| 7,090,755 B2 * | 8/2006 | Inoue et al. | 204/401 |
| 2003/0192781 A1 | 10/2003 | Kiesele et al. | |
| 2005/0121338 A1 * | 6/2005 | Inoue | 205/775 |

FOREIGN PATENT DOCUMENTS

| EP | 0 260 005 A2 | 3/1988 |
|---|---|---|
| EP | 0 260 005 A3 | 8/1990 |

OTHER PUBLICATIONS

European Search Report corresponding to Application No. EP 11 15 8603, dated Jun. 17, 2011. Jungil Park et al., "Microfabirated Clark-type Sensor for Measuring Dissolved Oxygen," Sensors, 2007 IEEE, IEEE, PI, Oct. 28, 2007.
PP. 1412-1415, XP031221337, ISBN: 978-4244-1261-7, *paragraph [III.A]; figure 4 *.
Extended European Search Report corresponding to European Patent Application No. 09157370.9, dated Jan. 19, 2010.

* cited by examiner

*Primary Examiner* — Jeffrey T Barton
*Assistant Examiner* — Louis Rufo
(74) *Attorney, Agent, or Firm* — Husch Blackwell LLP

(57) ABSTRACT

A method of operating an electrochemical gas sensor includes:
  a) exposing, for a first predetermined duration, the electrochemical gas sensor to an atmosphere containing a target gas while the gas reaction capability of the electrode assembly is substantially reduced from a working level, such that target gas is collected within the housing;
  b) increasing the gas reaction capability of the electrode assembly to a level at which it consumes collected target gas and thereby outputs a signal to the sensing circuit, including an initial transient decay signal;
  c) monitoring the transient decay signal; and
  d) analysing the rate of decay of the transient decay signal to determine whether the performance of at least one component of the electrochemical gas sensor is within acceptable limits.

An apparatus for operating an electrochemical gas sensor, adapted for connection to an electrochemical gas sensor via a sensing circuit for control thereof, can carry out the disclosed method(s).

16 Claims, 12 Drawing Sheets

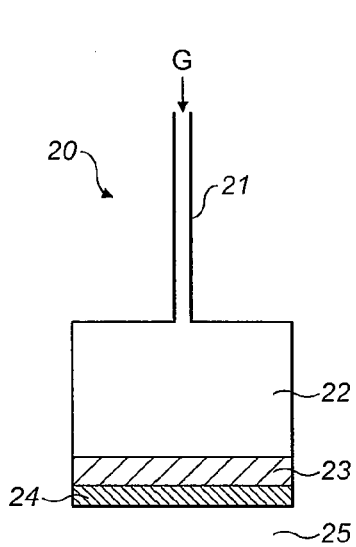
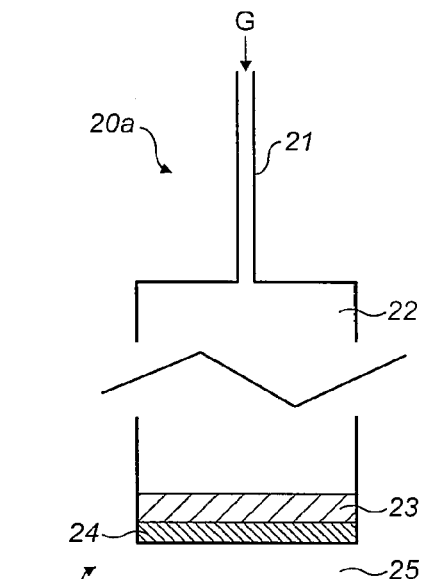
FIG. 3A    FIG. 3B
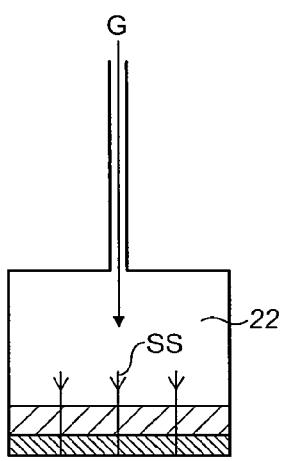
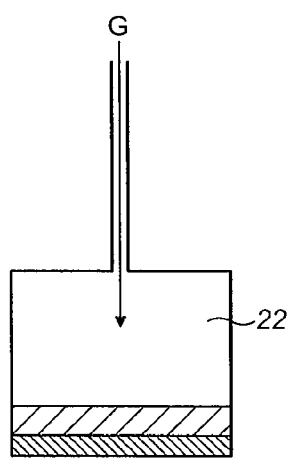
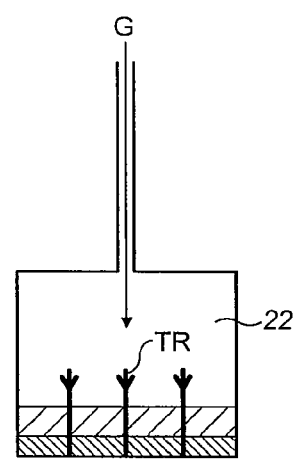
FIG. 4A    FIG. 4B    FIG. 4C

METHODS OF OPERATION OF ELECTROCHEMICAL GAS SENSORS

FIELD OF THE INVENTION

This invention relates to methods of operating an electrochemical gas sensor, which in particular can be used to determine whether certain components of the electrochemical gas sensor are performing within acceptable limits.

BACKGROUND OF THE INVENTION

Electrochemical gas sensors, such as oxygen sensors, are normally designed to operate in a diffusion limited mode. This is normally achieved by using a capillary or membrane, which limits gas access in a well defined and repeatable way. The sensor is designed such that the capillary or membrane provides the limiting factor. For example, the gas sensing electrode is designed to have sufficient activity reserve that the actual activity of the electrode can generally be ignored (since it is much greater than required to consume the available gas). Under certain conditions, however, sensors can deviate from the ideal diffusion limited behaviour: for example, if the catalytic activity of the electrode falls significantly, or if blocking or flooding of the membrane supporting the electrode occurs, then the sensor current may fall below the ideal diffusion limited current. In other cases, faults can occur with the diffusion limiting component, such as cracking or damage to the housing, resulting in a higher diffusion limited current, or conversely partial blocking of the capillary or diffusion limiting membrane can result in a lower diffusion limited current.

In addition to such faults which can result in a change in the level of gas response, certain faults can result in a reduction in the speed of response, even though the steady state response remains unchanged: for example, if the electrode-supporting membrane becomes partially flooded this causes initially a slow response, then in extreme cases a reduction in steady state response. The same is true if the catalytic activity of the electrode is reduced, which can be a particular problem for sensors with low activity reserve.

It is desirable to be able to detect and diagnose such faults, preferably with the sensor in a measuring instrument (i.e. in situ) and without user intervention. It is also desirable to be able to extract information about sensor parameters such as the catalytic activity, and the presence and correct operation of internal components, as an end of line production test for example. If such faults or changes in sensor performance can be reliably and simply detected, the resulting information could be used to indicate when maintenance is due, or to modify data processing algorithms to compensate for changes in performance, for example.

Some of the above mentioned faults or parameters can be detected by "gas testing" the sensor. Examples of such techniques are disclosed in EP-A-0260005, U.S. Pat. No. 6,165,347 and U.S. Pat. No. 5,741,413. In each case, a sensor to be calibrated is exposed to a known amount of gas and the resulting current produced by the sensor is analysed and used to calibrate the output, based on the known volume and/or concentration of gas. In EP-A-0260005 and U.S. Pat. No. 6,165,347, the test is conducted by filling a chamber of known volume with the test gas and exposing the sensor to the chamber. In U.S. Pat. No. 5,741,413 the tiny "dead" volume within the sensor itself is used as the test gas chamber, which is sealed (or has its communication with the external atmosphere much reduced) by the use of a valve mechanism which at least partially closes capillary access into the sensor.

However, gas testing the sensor in this way is often not feasible in the field, since access to sensors in situ may be difficult or even dangerous. In addition, such techniques require additional mechanical components, increasing the cost, size and complexity of the instrument. Further, the nature of the gas test is such that the sensor must be taken out of normal operation while it is exposed to the test gas, and remain so while the necessary measurements are taken. Moreover, such gas tests can only detect faults which are severe enough to take the sensor out of its normal diffusion limited operating regime. Likewise, U.S. Pat. No. 5,558,752 describes a method of determining whether a sensor signal is limited by diffusion or kinetics by determining whether the sensor current varies with the bias potential applied to the sensor.

U.S. Pat. No. 6,428,684 discloses a diagnostic technique in which the sensing circuit is momentarily broken while the flux of gas continues into the sensor. The short transient signal generated when the sensor is switched back on is compared with the steady state current and the time for which the sensor circuit was kept open, in order to determine whether the amount of gas consumed during the transient is equal to that which would be expected to be consumed had the reaction continued at its steady state level for the open circuit duration. Thus, the test is simply able to determine whether the sensor as a whole is operating under diffusion control or not. However, there are many scenarios in which, despite a fault, the sensor continues to operate under diffusion control and this test will not be able to identify such problems.

It is desirable to be able to measure such parameters which are normally masked by the diffusion limiting behaviour of the sensor. For example, in a sensor which is gradually losing catalytic activity, a gas test such as those described above will only detect this when the activity has become the limiting factor, which in many situations is too late. It is desirable to obtain an early warning of impending failure, for example by determining that the activity has fallen below a safe level (that level still being above the level needed for the sensor to be diffusion limited) or to monitor the change in activity over a time, to predict the remaining lifetime. Similarly, as previously mentioned, in new sensors, it is desirable to have a catalyst activity significantly higher than necessary in order to provide excess activity reserve to allow for loss of activity over the sensor lifetime and with effects such as varying temperature. It is desirable to be able to perform a simple end of line production test to check that the activity is within a certain range (again, while the sensor is diffusion limited). Conventional gas tests at ambient temperature on the assembled sensor will not allow this to be measured.

BRIEF DESCRIPTION OF THE DRAWINGS

Examples of methods and apparatus in accordance with the present invention will now be discussed with reference to the accompanying drawings, in which:

FIGS. 3 A and B show schematically an example of an electrochemical gas sensor in terms of some of its functional components;

FIGS. 4 A, B and C show the schematic electrochemical gas sensor of FIG. 3 during steps performed in accordance with embodiments of methods of controlling the operation of the gas sensor;

DETAILED DESCRIPTION

Figure 1:
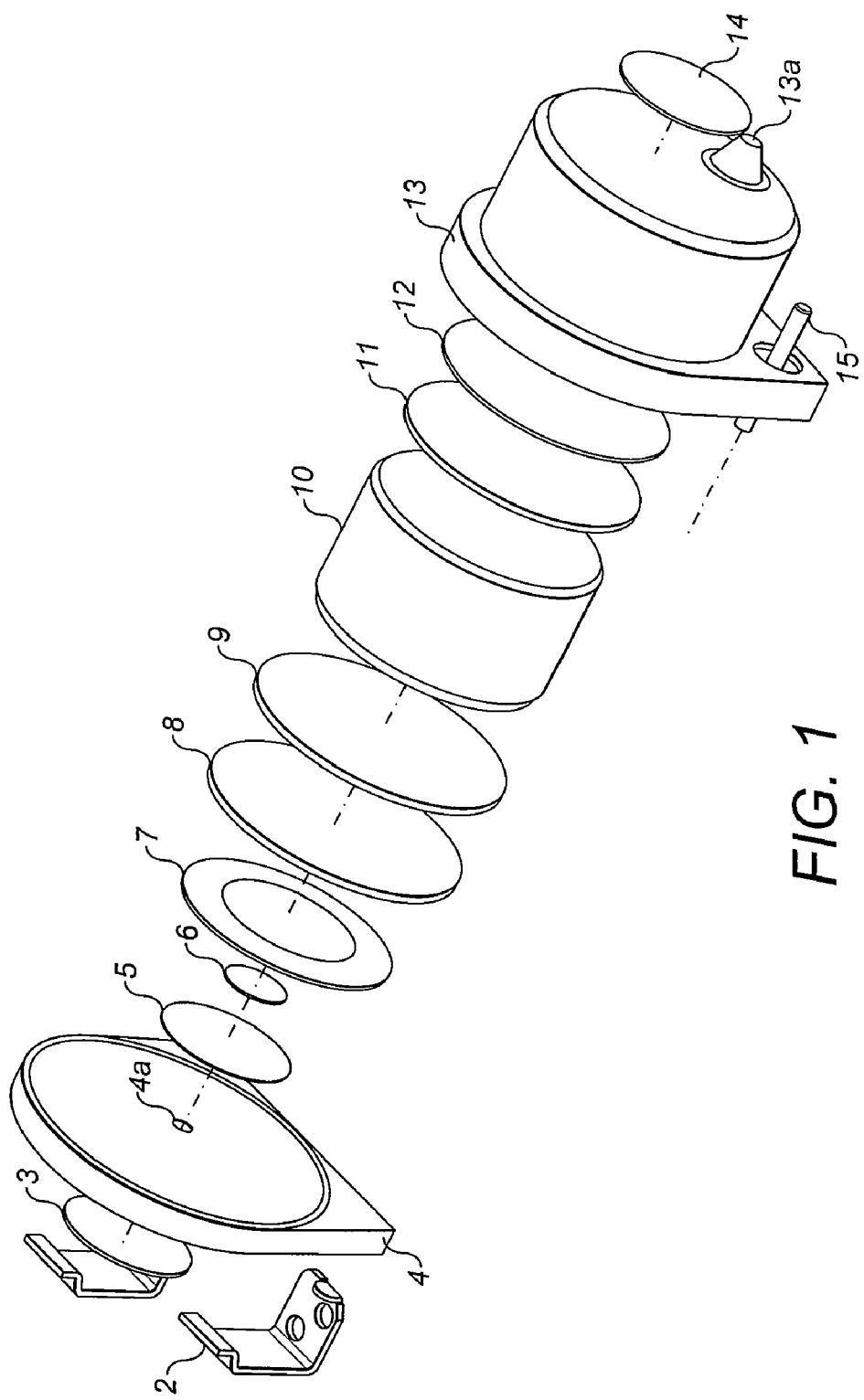
FIG. 1 is an exploded view showing an example of an electrochemical gas sensor.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

In accordance with a first aspect of the present invention, a method of operating an electrochemical gas sensor is provided, the electrochemical gas sensor comprising an electrode assembly disposed within a housing having a diffusion limiting barrier for gas ingress therethrough, the electrode assembly comprising a gas sensing electrode, a counter electrode, and electrolyte in fluid communication with the gas sensing and counter electrodes, and the electrochemical gas sensor further comprising connectors for connecting the gas sensing and counter electrodes to a sensing circuit, the method comprising:

a) exposing, for a first predetermined duration, the electrochemical gas sensor to an atmosphere containing a target gas while the gas reaction capability of the electrode assembly is substantially reduced from a working level, such that target gas is collected within the housing;

b) increasing the gas reaction capability of the electrode assembly to a level at which it consumes collected target gas and thereby outputs a signal to the sensing circuit, including an initial transient decay signal;

c) monitoring the transient decay signal; and d) analysing the rate of decay of the transient decay signal to determine whether the performance of at least one component of the electrochemical gas sensor is within acceptable limits.

By reducing or even halting the gas reaction, gas is collected within the sensor housing, which can be used to diagnose faults in the sensor without the need for user intervention. In particular, there is no need to provide a known volume of test gas, or indeed test gas of any sort, provided a measurable quantity of the target gas is normally present in the atmosphere. When the reaction resumes, there is an initial transient decay signal as the collected gas is consumed, returning to the steady state current level once the excess gas has been consumed. This transient decay signal is monitored and its rate of decay analysed, from which the performance of components within the electrochemical gas sensor can be assessed. It should be noted that the transient decay signal may not be a conventional linear or exponential decay since it can be complicated by various factors, and so may be analysed by calculating gradients, time constants, curve comparisons or any other suitable technique. Nonetheless, by looking at the rate of decay of the transient decay signal, as opposed to the amount of consumed gas to which this corresponds, it becomes possible to obtain more information than simply whether the sensor as a whole is operating under diffusion control. In particular, the performance of components which affect the time dependency of the reaction can be investigated. For example, as described below, it becomes possible to assess whether the electrode assembly is operating correctly, both in terms of its diffusive and kinetic behaviour, and to distinguish between the two if a problem is identified. Moreover, by analysing the rate of decay of the transient decay signal, the test is independent of the behaviour of components which affect gas diffusion into the sensor such as the diffusion limiting barrier, or the housing itself. Thus, it becomes possible to diagnose specific faults in the components which control the reaction performance of the sensor, and separate them from faults relating to gas control elements.

The method can be used to determine the performance of certain components within the electrochemical gas sensor in isolation (i.e. irrespective of the performance of other components of the gas sensor), although these components may include sub-assemblies, each comprising more than one individual part, such as the electrode assembly. Preferably, in step d), it is determined whether the diffusive and kinetic behaviour of the electrode assembly is within acceptable limits. Advantageously, this is achieved by determining a rate of decay of the transient decay signal versus time, to thereby obtain a combined measure of the activity of the gas sensing electrode and level of gas access to the gas sensing electrode. For example, the determined rate of decay could be compared with a pre-set scale to judge the general performance of the gas sensing electrode, both in terms of its diffusive and kinetic behaviour.

Preferably, step d) further comprises comparing the determined rate of decay with a predetermined rate of decay to determine whether in combination the activity of the gas sensing electrode and level of gas access to the gas sensing electrode are within acceptable limits. This enables a decision to be taken as to whether the electrode assembly is operating adequately or whether further investigation is required.

To distinguish between diffusive and kinetic faults, in a particularly preferred embodiment, in step (b), the gas reaction capability of the electrode assembly is increased by applying a first bias potential to the gas sensing electrode, and after at least step (c) is performed, steps (a), (b) and (c) are repeated;

wherein, when step (b) is repeated, the gas reaction capability of the electrode assembly is increased by applying a second bias potential to the gas sensing electrode, the second bias potential being different to the first, to thereby determine in step (d) a variation of the transient decay signal with applied bias potential and so determine whether the reaction at the gas sensing electrode is diffusion limited or kinetically limited.

In two-electrode sensors, the bias voltage is between the sensing and counter electrodes, whereas in three-electrode circuits, the bias voltage is between the sensing and reference electrodes.

In general, changing the bias potential applied to a sensor changes the rate at which target gas is consumed and hence the "slope" of the decay transient. However, for each sensor, there will be a range of bias voltage values within which a change in voltage will not cause a change in the transient decay signal. This occurs when the sensor is operating in a diffusion controlled regime where the reaction capability of the electrode is sufficiently high that the rate of gas reaction is limited by the rate of gas arriving at the electrode, rather than by the reaction itself. Note that the diffusion limitation described here is not the capillary or membrane that provides diffusion limitation of the sensor under normal operation, as this component has effectively been bypassed by performing the open circuit cycle. The diffusion limitation could be, for example, due to the membrane supporting the electrode or the thin layer of electrolyte which the gas must pass through to reach the electrode. By assessing the variation of the transient decay signal with applied bias potential, it can be determined which regime the electrode is operating in and so establish whether the fault is due to a loss of activity or a shift in the electrode potential (both examples of problems leading to kinetic limitation), or reduced gas diffusion (e.g. due to flooding of the electrode by the electrolyte). Preferably, steps a), b) and c) are repeated a plurality of times over a range of different bias potentials applied in step b) to thereby determine in step d) a variation of the transient decay signal with applied bias potential. The greater the number of different applied bias voltages used, the better the accuracy of the technique.

Advantageously, the applied bias voltage is controlled using a two electrode potentiostat circuit, a three electrode potentiostat circuit or a current follower circuit. Any other suitable technique for controlling the applied voltage could be used instead.

In a further example, the applied bias voltage is controlled by connecting the gas sensing and counter electrodes in series with a first fixed-value load resistor and then, when steps a), b) and c) are repeated, in series with at least a second fixed-value load resistor of different resistance, such that a bias voltage is generated across each load resistor in turn, the magnitude of the bias voltage varying in accordance with the resistance of each load resistor. It should be noted that the second fixed value load resistor could include the first fixed value load resistor (i.e. the second fixed value load resistor could comprise more than one load resistor in series, one of which may be the first fixed value load resistor). The magnitude of the bias voltage generated as a result of the current from the sensor will depend on the magnitude of the resistance, in accordance with Ohm's law, thus providing a simple yet effective means of varying the applied bias voltage. The sensing circuit can be switched between different fixed value load resistors (or combinations thereof) between repetitions of steps a), b) and c).

In another preferred embodiment, the applied bias voltage is controlled by connecting the gas sensing and counter electrodes in series with a variable-resistance load resistor, the resistance of the load resistor being adjusted between at least a first value and, when steps a), b) and c) are repeated, a second value, such that a bias voltage is generated across the variable-resistance load resistor, the magnitude of the bias voltage varying in accordance with the resistance. The variable resistance load resistor could take the form of a transistor or solid state potentiometer, for example. The magnitude of the resistance could be adjusted between repetitions of steps a), b) and c).

The above embodiments apply mainly to two-electrode sensors, and in particular consumable anode oxygen sensors. However the technique is equally applicable to three-electrode sensors which contain a reference electrode in addition to the sensing and counter electrode and which are normally operated in a potentiostat circuit. In such circuits, the bias voltage is established between the sensing and reference electrodes (although it is controlled by applying a voltage between the sensing and counter electrodes as described above). For example the technique may be applied to either toxic gas sensors or 'oxygen pump' sensors, based on liquid or solid electrolyte fuel cell type designs. In this case the 'open circuit' phase may be achieved by physically opening the connection to the working or reference electrode, or alternatively the bias voltage may be adjusted to a value where the sensor current falls to zero—either by setting the bias to a suitable predetermined fixed value, or by actively adjusting the bias such that the current is zero.

In the aforementioned techniques, the decay transient resulting from each different bias voltage is analysed to determine the variation of the decay transient with bias voltage. However, in another preferred embodiment, only a single transient measurement is needed to obtain and discriminate kinetic and diffusional information. In this case, in step (b), the gas reaction capability of the electrode assembly is increased by applying a bias potential between the gas sensing electrode and the counter electrode, the bias potential varying during the decay transient signal and, in step (d), measurements from at least two portions of the decay transient signal corresponding to different applied bias potentials are taken to determine a variation of the transient decay signal with applied bias potential and so determine whether the reaction at the gas sensing electrode is diffusion limited or kinetically limited.

By varying the bias potential during the decay transient signal and looking at different portions of the signal, it is possible to assess whether the change in bias potential is affecting the rate of decay of the transient and so determine whether the sensor is diffusion or kinetically limited as before. Since only a single decay transient curve need be obtained, the necessary information can be obtained from a single cycle of steps a), b), c) and d), without the need for repeating the process. The analysis is thus faster and less out-of-service time is required.

This adjustment technique can also be implemented in a number of ways. In a preferred embodiment, the bias potential is allowed to vary by connecting the gas sensing and counter electrodes in series with a fixed-value load resistor of sufficient resistance such that the bias voltage is generated across the load resistor and the magnitude of the bias voltage decreases as the transient current output by the electrodes decreases. The use of a load resistor in this way effectively allows the bias voltage to vary as a function of the sensor current. The bias voltage starts off high when the transient current is high, then as the current decays as the collected gas is consumed, the bias voltage decreases in proportion. The electrode kinetics therefore increase over time during the transient decay curve, and the gradient of the transient (i.e. the rate of oxygen consumption) will change over time, but only where the sensor is not operating in the diffusion limited regime. This technique is straightforward to implement electronically, requiring simply a fixed load resistor of sufficient resistance that a current dependent external bias voltage is generated. For example, a load resistor of around 10 ohms may be suitable, which will result in a bias voltage of 100 millivolts at 10 milliamps, but has negligible effect under normal steady state conditions where the sensor current is typically hundreds of microamps or less. Consumable-anode oxygen sensors are often operated into such a load resistor, so the modifications required to the circuit to perform the transient measurement are minimal.

In an alternative preferred embodiment, the applied bias voltage is controlled by connecting the gas sensing and counter electrodes in series with a first fixed-value load resistor and then, during the decay transient signal, in series with at least a second fixed-value load resistor of different resistance, such that a bias voltage is generated across each load resistor in turn, the magnitude of the bias voltage varying in accordance with the resistance of each load resistor. As in the case discussed above, either or both fixed value load resistors may in practice comprise a combination of more than one fixed value load resistor in series.

In another preferred implementation, the applied bias voltage is controlled by connecting the gas sensing and counter electrodes in series with a variable-resistance load resistor, the resistance of the load resistor being adjusted between at least a first value and a second value during the decay transient signal, such that a bias voltage is generated across the variable-resistance load resistor, the magnitude of the bias voltage varying in accordance with the resistance. Any form of actively adjustable load resistor could be selected, such as a transistor or a solid state potentiometer. Such devices can either be pre-set to a particular resistance (or I/V characteristic value) or can actively be adjusted in a form of potentiostat circuit to maintain a constant or varying bias voltage as required.

Preferably, if in step d) it is determined that the transient decay signal varies substantially with applied bias potential within a predefined bias potential range, it is concluded that the reaction at the gas sensing electrode is kinetically limited. Conversely, if in step d) it is determined that the transient decay signal substantially does not vary with applied bias potential within a predefined bias potential range, it is concluded that the reaction at the gas sensing electrode is diffusion limited.

The above techniques may also be adapted for use with a three electrode sensor—either by simply ignoring the reference electrode and running the sensor as a two electrode sensor, or in the case where an actively adjustable load resistance is used, this could be adjusted within a three electrode potentiostat circuit to obtain the desired bias voltage between sensing and reference electrodes.

These bias voltage varying techniques can also be used to give an indication as to the health of the gas sensing electrode, and predict whether failure is likely to occur soon. Therefore, preferably, in step d), the determined variation of the transient decay signal with time is analysed to identify at what applied bias voltage a substantial change in the rate of decay of the transient decay signal is first observed to thereby obtain a measure of the activity of the gas sensing electrode. The identified applied bias voltage can be compared with predetermined levels to ascertain whether the sensor is close to failure. Alternatively or in addition, if the test is repeated over a period of time, the identified applied bias voltages can be tracked and compared with one another to determine how the activity of the gas sensing electrode is changing.

As mentioned above, analysing the rate of decay of the transient decay signal can be used to provide information about various components within the gas sensor which affect the rate of reaction. In another particular preferred embodiment, the electrochemical sensor further comprises a bulk flow membrane arranged to restrict bulk flow of gas into the housing and, in step d), it is determined whether the diffusive behaviour of the bulk flow membrane is within acceptable limits. It should be noted that a bulk flow membrane does not affect diffusive gas ingress to the sensor but rather prevents bulk flow ingress of gas. Hence its performance does not affect gas ingress in normal, "steady state" operation and the membrane is not classed as a gas diffusion element. However, during the decay transient, the increased current can lead to a scenario in which the rapidly decreasing concentration of target gas within the sensor increases the drive for ingress of the target gas (in order to attain equilibrium). If operating well, the bulk flow membrane should substantially prevent this extra ingress of target gas. If not, this will be apparent from the shape of the decay curve.

Preferably, in step d), the rate of decay of the transient decay signal is determined and compared with predetermined rates of decay indicative of bulk gas flow into the sensor in order to determine whether the diffusive behaviour of the bulk flow membrane is within acceptable limits.

In accordance with a second aspect of the present invention, a method of operating an electrochemical gas sensor is provided, the electrochemical gas sensor comprising an electrode assembly disposed within a housing having a diffusion limiting barrier for gas ingress therethrough, the electrode assembly comprising a gas sensing electrode, a counter electrode, and electrolyte in fluid communication with the gas sensing and counter electrodes, and the electrochemical gas sensor further comprising connectors for connecting the gas sensing and counter electrodes to a sensing circuit, the method comprising:

a) exposing, for a first predetermined duration, the electrochemical gas sensor to an atmosphere containing a target gas while the gas reaction capability of the electrode assembly is substantially reduced from a working level, such that target gas is collected within the housing;

b) increasing the gas reaction capability of the electrode assembly to a level at which it consumes collected target gas and thereby outputs a signal to the sensing circuit, including an initial transient decay signal;

c) monitoring the transient decay signal;

d) repeating steps (a), (b) and (c) wherein, when step (a) is repeated, the gas sensitive electrode is exposed to the atmosphere for a second predetermined duration different from the first predetermined duration; and e) analysing the dependency of the transient decay signal on the duration of gas collection in step (a) to determine whether the performance of at least one component of the electrochemical gas sensor is within acceptable limits.

Preferably, in step e) it is determined whether the diffusive behaviour of the diffusion limiting barrier is within acceptable limits.

By varying the time for which target gas is collected by the sensor such that the dependency of the transient decay signal and the duration of gas collection can be determined, it is possible to investigate the behaviour of the diffusion limiting barrier separately from that of the components contributing to the reaction within the sensor. As such, the performance of the diffusion limiting barrier can be judged whether or not there is also a fault within the electrode assembly. It should be noted that none of the conventional gas testing techniques described above make root cause diagnosis of faults affecting gas ingress into the sensor possible.

Preferably, steps (a), (b) and (c) are repeated a plurality of times over a range of different predetermined durations for which the gas sensitive electrode is exposed in step (a). The greater the number of repetitions at different durations, the better the accuracy of the diagnostic test.

Preferably, in step (e), the transient decay signal for each predetermined duration is integrated over time, the result corresponding to a charge representing the amount of gas consumed during the transient decay signal, and the variation of the charge with duration of gas collection is determined, from which it is determined whether the diffusive behaviour of the diffusion limiting barrier is within acceptable limits. Preferably, in this process, substantially the whole transient decay signal is integrated, up until the signal returns to its steady state level. The area under the transient decay signal corresponds to the charge evolved by the reaction of the gas on the electrodes which is related directly to the amount of gas which has been collected during step (a). The variation of the charge with duration of gas collection therefore provides a measure of the diffusive behaviour of the diffusion limiting barrier.

In a particularly preferred embodiment, the method further comprises extrapolating the determined variation to infinite gas collection duration to thereby determine a charge corresponding to collected target gas at equilibrium with the surrounding atmosphere. As described in more detail below, this makes it possible to take an independent absolute measure of target gas concentration in the atmosphere, which can be used not only for sensor calibration but also, in combination with other analysis techniques, to assess the performance of sensor components. The extrapolation could be performed, for example, by performing a number of measurements at different open circuit times and curve fitting to calculate the charge at infinite time.

Preferably, the method further comprises measuring the gradient near the origin of a plot of integrated total charge versus duration of gas collection and comparing the gradient with the steady state current of the electrochemical gas sensor to determine whether the diffusive behaviour of the diffusion limiting barrier is within acceptable limits. The measured gradient corresponds to the ideal steady state current value of the sensor when operating under diffusion control. If a comparison reveals that the determined gradient is greater than the actual steady state current value (measured from the sensor prior to the open circuit period or after recovery from the transient, for example), it is deduced that the sensor current is not limited by the behaviour of the diffusion limiter. This could be the case if, for example, the diffusion limiter is damaged such that access of gas can occur at a rate exceeding that at which it can be consumed by the sensing electrode, or if the activity of the electrode were sufficiently reduced. If on the other hand the determined gradient is less than the predetermined steady state current, this implies that there is an additional source of current within the sensor. This could be the case if, for example, there is a source of gas bypassing the diffusion limiter and dead volume, or if there is a background current in the absence of target gas, due for example to contamination by electroactive species within the electrolyte. If the determined gradient is substantially equal to the actual steady state current value, this reveals that the diffusion limiting barrier is operating as the main diffusion limiter.

As an alternative, or in addition, the method preferably further comprises extrapolating the determined variation of charge with duration of gas collection to determine the level of charge where the duration of gas collection is zero, in order to determine whether the behaviour of the electrode assembly is within acceptable limits. Ideally, where the duration of gas collection is zero, the concentration of collected target gas within the sensor is zero and hence there should be no decay transient and hence zero charge. This will be the case if the sensing electrode is sufficiently active that under normal operating conditions it consumes all of the target gas entering the sensor, with the result that the concentration of gas at the inner face of the capillary or diffusion limiting membrane is zero. However, if the electrode is not sufficiently active, then there will be a finite concentration of target gas present in the sensor housing between the capillary and electrode even under normal operating conditions. This will therefore give rise to an additional 'offset' in a plot of charge vs. open circuit time, i.e. extrapolation of such a curve to zero open circuit time will give a value greater than zero.

As mentioned above, it is useful to obtain an independent, absolute measure of target gas concentration in the atmosphere to which the sensor is exposed, i.e. without requiring calibration or knowledge of the diffusion limitation of the barrier or the catalytic activity of the electrode, and this is preferably achieved by extrapolating the measured dependence on open circuit time to infinite time. In alternative embodiments, however, it is preferred that step a) is performed at least once for a predetermined duration which is sufficient for the collected gas to substantially equilibrate with the atmosphere to which the sensor is exposed, under diffusion conditions. This technique allows for a higher degree of accuracy but potentially takes the sensor out normal operation for a longer period of time.

Whichever technique is employed, by determining the charge at long collection times, where the gas within the sensor housing has substantially equilibrated with the external atmosphere, it becomes possible to obtain an absolute measure of gas concentration in the external atmosphere. This absolute measure can then be used for calibration of the sensor. Further, it is possible to measure the ideal steady state current of the sensor without knowledge of the sensor volume, diffusion performance or other variables. A particular benefit is that the independent absolute measure of target gas concentration can be used in conjunction with either the steady state signal of the sensor, or the integrated transient measurements described above, to determine whether the diffusion limiter itself is operating correctly—i.e. leading to a diffusion limited steady state current of the correct magnitude. For example, this could be used to identify whether a capillary is of the correct dimension, or is blocked or cracked.

In accordance with a third aspect of the present invention, a method of operating an electrochemical gas sensor is provided, the electrochemical gas sensor comprising an electrode assembly disposed within a housing having a diffusion limiting barrier for gas ingress therethrough, the electrode assembly comprising a gas sensing electrode, a counter electrode, optionally a reference electrode, and electrolyte in communication with the electrodes, and the electrochemical gas sensor further comprising connectors for connecting the electrodes to a sensing circuit, the method comprising:

a) exposing, for a first predetermined duration, the electrochemical gas sensor to an atmosphere containing a target gas while the gas reaction capability of the electrode assembly is substantially reduced from a working level, such that target gas is collected within the housing;

a1) monitoring the potential difference between the gas sensing electrode and the counter or reference electrode over time as the first predetermined duration elapses; and a2) analysing the monitored potential difference to determine whether the performance of at least one component of the electrochemical gas sensor is within acceptable limits.

The potential difference evolved between the electrodes during the period of reduced, preferably zero, gas reaction capability depends on the concentration of the target gas in the dead volume within the sensor. By monitoring this voltage during the "open circuit" time, information about the rate of filling of the dead volume can therefore be obtained.

Preferably, step a2) comprises determining the time dependency of the monitored potential difference, and comparing the determined time dependency with a predetermined value to determine whether the diffusion limiting barrier is performing within acceptable limits. This is a straightforward technique for determining whether the barrier is allowing gas ingress at the expected rate.

In other preferred embodiments, step a2) comprises extrapolating the monitored potential difference to infinite gas collection duration, to obtain a measure of the target gas concentration in the atmosphere. This measure can be used in a number of ways, including self-calibration of the sensor.

Advantageously, the measure of target gas concentration in the atmosphere is used to determine a diffusion limitation factor of the diffusion limiting barrier. For example, in the case of a capillary barrier this can be used to determine whether its dimensions are of the correct size.

In a particularly preferred embodiment, the method further comprises:

b) increasing the gas reaction capability of the electrode assembly to a level at which it consumes collected target gas and thereby outputs a signal to the sensing circuit, including an initial transient decay signal;

c) monitoring the transient decay signal; and d) integrating the monitored transient decay signal to obtain a measure of charge corresponding to the collected target gas, and calibrating the monitored potential difference using the obtained measure of charge.

The integrated measurement provides an "absolute" measurement of the gas collected during step a) and so can be used to improve the accuracy of the results taken from the potential monitored in step a1).

In the methods according to the first, second or third aspects of the invention, in step a) the gas reaction capability of the electrode assembly need not be reduced to zero but must be low enough to allow target gas to be collected within the housing. However, preferably, during step a) the electrode assembly is substantially inactive, such that substantially no target gas is consumed. Reduction of the gas reaction capability may be achieved in a number of ways. In one preferred embodiment, in step a), the sensing circuit is open, such that no electric current can flow between the gas sensing and counter electrodes. In another preferred example, in step a), a suitable bias potential is applied between the gas sensing encounter electrodes by the sensing circuit to reduce the gas reaction capability of the electrode assembly.

Similarly, in step b) the gas reaction capability of the electrode assembly may be increased in a number of different ways. In a first preferred example, the sensing circuit is closed in order to allow electric current to flow between the gas sensing encounter electrodes. In another preferred example, the bias potential applied to the electrode assembly by the sensing circuit is changed such that the reaction increases.

Methods in accordance with the invention could be implemented using cyclic voltammetry techniques. In a particularly preferred example, steps (a) and (b) are performed by cycling a bias potential applied between the gas sensing and counter electrodes between a working value and an open circuit potential, the predetermined duration of exposure being defined as the duration for which the applied potential is within a first predetermined range including the open circuit potential, during which consumption of the target gas by the gas sensing electrode is low, and the transient decay signal being monitored once the applied potential is within a second predetermined range including the working value. This cycle could be performed a single time or a plurality of times as necessary. The technique could also be used in conjunction with previously described methods of varying bias potential and/or the open circuit time by adjusting the level of the open circuit potential between cycles and/or adjusting the timing of the cycling.

Preferably, the bias potential applied between the gas sensing and counter electrodes is held at the open circuit potential for a specified time forming part of the predetermined duration of exposure.

Advantageously, the diffusion limiting barrier comprises a capillary or a diffusion limiting membrane.

Preferably, the methods of the first, second and/or third aspects of the invention are applied to an electrochemical gas sensor in situ at a sensing location and the method further comprising:

i) prior to step a), reducing the gas reaction capability of the electrode assembly from a working condition; and ii) after at least step a), restoring the gas reaction capability of the electrode assembly to the working condition, or to a different working condition.

The disclosed technique can therefore be used with a minimum of disruption to the usual monitoring regime.

In certain preferred examples, the method is repeated at predefined intervals. For example, the test could be performed regularly after a certain number of minutes or hours has elapsed, or weekly, monthly or annually for example.

In another preferred implementation, step (i) is performed by switching off the electrochemical gas sensor, and the other steps of the method are performed when the electrochemical gas sensor is next switched on. As such, the diagnostic tests of the present invention would be performed automatically upon each start up of the sensing device.

The present invention further provides apparatus adapted to perform the method in accordance with the first, second and/or third aspects of the present invention, the apparatus comprising a processor that is to be connected to the sensing circuit for control thereof, the processor being programmed to perform the aforementioned steps. In a particularly preferred example, the processor could be incorporated into a docking station to which a sensing device incorporating the electrochemical gas sensor can be coupled, either as an in situ mounting, or for storage of the sensing device when not in use. The docking station may also include recharging facilities, for example. In another example the processor could be integrated into the sensing device itself.

The invention also provides a computer program product containing instructions for performing any of the method(s) described above. This could comprise, for example, a microprocessor, disk, CD-ROM, memory stick, hard drive or any other storage device on which instructions for performing the method(s) are retained (in the form of software, firmware or hardware), to be performed for example by a computer or other processor (including, where appropriate, the computer program product itself) which is supplied with the instructions.

It should be noted that any of the disclosed methods may be used either alone or in combination with one another.

Methods and apparatus in accordance with the present invention can be used in conjunction with any type of electrochemical gas sensor, including consumable anode oxygen sensors, oxygen pumps and toxic gas sensors. However, in practice the techniques are most likely to be implemented in oxygen sensors, since in order for the measurements to be taken, it is necessary for the target gas which the sensor is designed to detect to be present in the atmosphere to which the sensor is exposed. In most scenarios the presence of toxic gas in the ambient atmosphere is highly undesirable, although if the sensor is deployed in an environment which is not to be accessed by personnel (e.g. inside machinery or another enclosure) this may not be the case and the presently disclosed techniques could be applied. Other examples of sensors to which the methods might readily be applied are carbon dioxide sensors, since ambient levels of $CO_2$ are generally sufficient for measurement, and ammonia sensors used for example in poultry farms where a significant level of the target gas is usually present. Nonetheless, the following description will focus on the example of an oxygen sensor since this is a primary application of the technique.

Amperometric electrochemical oxygen sensors traditionally comprise a gas diffusion working electrode (Agas-sensing electrode@), often based on a graphite/platinum catalyst dispersed on PTFE tape. Oxygen is reduced at this cathode according to the reaction:

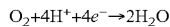

$$O_2 + 4H^+ + 4e^- \rightarrow 2H_2O$$

while a balancing oxidation takes place at a consumable anode (Acounter electrode@), most frequently made of lead (Pb):

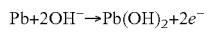

$$Pb + 2OH^- \rightarrow Pb(OH)_2 + 2e^-$$

The electrodes are held within an outer housing which contains a liquid electrolyte capable of supporting the relevant reactions, such as aqueous potassium acetate. The gas under test typically enters the housing through a controlled diffusion access which regulates the ingress of oxygen into the cell. By arranging that all oxygen is reacted at the cathode, the electrical output of the sensor may be directly related to the ambient oxygen concentration. Such principles are well known and have been described for example in 'Liquid Electrolyte Fuel Cells', B S Hobbs, A D S Tantram and R Chan-Henry, Chapter 6 in 'Techniques And Mechanisms In Gas Sensing', Eds P T Moseley, J O W Norris and D E Williams, Adam Hilger, 1991.

Unlike consumable anode oxygen sensors, electrochemical 'oxygen pump' sensors (to which the presently-disclosed methods are equally applicable) utilise a non-consumable counter electrode which evolves oxygen. This type of sensor needs to be operated with a bias voltage to drive the oxygen reactions, and will commonly be configured as a three-electrode device with the third electrode being a reference or pseudo-reference electrode. In this type of configuration the bias potential applied to the sensing electrode is relative to the reference electrode, with the sensor current being driven between the sensing and counter electrodes.

Figure 2A:
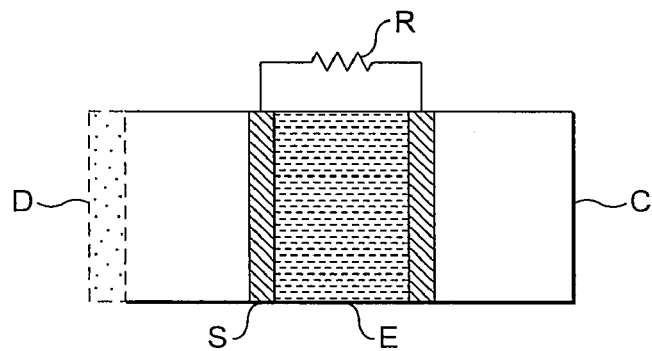
FIGS. 2 A, B and C are schematic diagrams showing three exemplary sensing circuits for use with an electrochemical gas sensor.
Figure 2B:
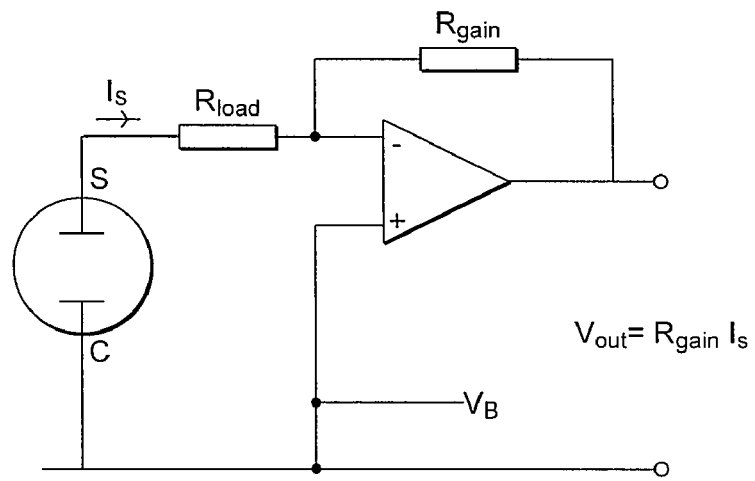
Figure 2C:
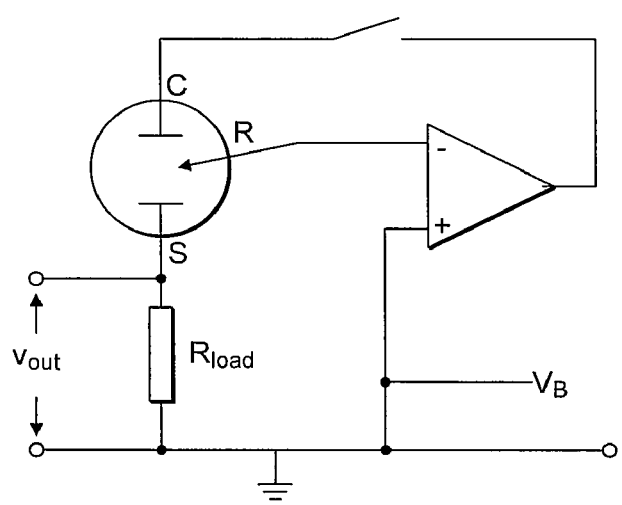

An example of a consumable anode oxygen sensor 1 (the MICROceL™ oxygen sensor produced by City Technology Ltd of Portsmouth, UK) is shown in FIG. 1. The oxygen sensor 1 comprises a housing formed of lid 4 and body 13, which when assembled, are joined to one another (e.g. by ultrasonic welding) and contain the electrode assembly therewithin. Lid 4 includes an aperture 4a therethrough for gas ingress, typically comprising a capillary and/or diffusion barrier membrane in order to limit the amount of gas entering the sensor. The electrode assembly essentially comprises a gas sensing electrode 7 and a counter electrode 10, each of which is electrically connected in use to a sensing circuit, for example via conductive connection pins 15 and contact clips 2. FIG. 2 shows three examples of conventional sensing circuits in which the sensor 1 could operate. FIG. 2a shows a basic schematic circuit in which the sensing electrode S (=gas sensing electrode 7) and counter electrode C (=anode 10) are connected with a load resistor R between them. The electrolyte E provides ionic communication between the two electrodes while gas access to the sensing electrode is controlled by diffusion barrier D. In use, the current passing through load resistor R is monitored to determine the concentration of target gas reacting at the sensing electrode. In practice, a two-electrode potentiostatic circuit, or current follower, such as that shown in FIG. 2b may be used. The three-electrode circuit shown in FIG. 2c is more often used with certain toxic gas sensors which employ separate reference and counter electrodes, as well as oxygen pump sensors. It will be appreciated that in these circuits, the load resistor is optional, and if included, generally should have a sufficiently low value that it does not give rise to a significant potential drop. However, the load resistor can also be used to intentionally produce a current-dependent bias voltage, as described in more detail below, in which case a higher value resistance is required. Alternatively and/or in addition, in all three circuits in FIG. 2 the sensor may be operated at a bias potential, achieved in the case of FIG. 2a by adding a suitable voltage source in series with resistor R, and in the case of FIGS. 2b and 2c by applying a bias voltage $V_B$ to the non-inverting input of the operational amplifier. Some types of sensor, particularly oxygen pump types, require such a bias voltage for normal operation. Further information concerning suitable signal measurement techniques may be found in chapter 6 of "Techniques and Mechanisms in Gas Sensing", cited above.

In use, the gas sensing electrode 7 and counter electrode 10 are each in contact with a liquid, solid or gel electrolyte, for example aqueous potassium acetate or another ionically conducting electrolyte. The electrolyte is contained within a cavity defined by housing body 13, which also holds the counter electrode 10. Separator layers 8, 9 and 11, which are electrolyte-permeable, may be provided above and below the counter electrode 10 in order to supply electrolyte to the gas sensing electrode 7 while preventing direct contact between the gas sensing and counter electrodes. The separators may be made of glass fibre, for example.

The gas sensing electrode 7 typically comprises a catalyst such as platinum or carbon, supported on a PTFE membrane. Conductive leads (not shown) are provided to electrically connect the catalytic area to the connection pins 15. The counter electrode 10 here takes the form of a consumable anode which will be oxidised as the cell reaction progresses. Typically, the anode 10 comprises a volume of porous material, such as lead wool, having a large surface area so as to avoid early passivation of the material.

In other sensor types, such as toxic gas sensors, the counter electrode may comprise a catalyst mounted on a PTFE backing tape, in the same manner as the gas sensing electrode 7.

The sensor 1 may also include a number of optional components, such as:
- a bulk flow disc 6, adhered to the inside of lid 4 by an adhesive disk 5. The bulk flow disk may be provided in order to restrict bulk flow of gas into the sensor and in particular reduce pressure transients and temperature-induced pressure transients.
- a vent 13a and vent membrane 12. As detailed in WO-A-04/031758, a vent 13a may be provided in the form of an aperture through the body of the cavity in order to assist in the avoidance of pressure differentials by enabling the passage of gas into and out of the sensor 10. To prevent escape of liquid through the vent, a gas porous but electrolyte impermeable (e.g. PTFE) membrane 12 may be provided. This is typically heat-sealed to the interior of the body 13. To avoid gas access through the vent becoming obstructed should the anode expand during operation (e.g. due to oxidation), the counter electrode 10 may be spaced from the vent by providing the electrode 10 with a recess.
- outboard of the sensor housing 4/13, a dust membrane 3 and vent protection membrane 14 may be provided to prevent the aperture 4a and vent 13a from dust and moisture.

Schematic drawings of a capillary limited oxygen sensor 20 are shown in FIGS. 3 A and B. Ideally, the signal output by the sensor should be limited solely by the amount of gas G which is allowed into the sensor by the capillary 21. In practice, it is possible for the signal to be partially limited by diffusional restriction of the electrode membrane 23 (e.g. if it becomes flooded with electrolyte 25). Under normal operation it is not possible to determine whether the sensor is giving a low output because it is actually seeing a low oxygen concentration, or because of some fault within the sensor such as a partially blocked capillary 21, a flooded membrane 23 or reduced activity of the gas sensing electrode, for example. Also, some faults such as membrane flooding and reduced activity may result in the 'correct' steady state signal but a dangerously slow response. Again, this is not easy to detect in the field. The present invention provides a way of separating out the sensor behaviour into two parts, as shown in FIG. 3 B. Using the techniques now disclosed, it is possible to investigate independently:
  i) Diffusion of gas through the capillary 21 into the dead volume 22 (illustrated as 20a); and
  ii) Consumption of gas by the electrode 23/24 (illustrated as 20b). Therefore parameters relating to gas diffusion into the sensor, such as the capillary, can be interrogated separately from parameters relating to the behaviour of the electrode assembly, such as diffusional restriction of the membrane and kinetics of the electrode reaction.

Under normal "steady state" operation, oxygen sensors continually consume oxygen, with the result that the oxygen concentration in the dead volume 22 between sensing electrode 23/24 and the capillary 21 (or other diffusion barrier) is virtually zero. This is illustrated in FIG. 4A where the arrows "SS" represent steady state consumption of the gas within dead volume 22, and indicate that the rate of consumption at the electrode is fast compared to the rate of diffusion through the capillary.

In embodiments of the present invention, in a first step, the ability of the sensor to consume gas is disabled (or at least repressed) for a period of time. This can be achieved by taking the sensor "off load" (i.e. open circuit-breaking the sensing circuit such that no electric current can flow between the gas sensing and counter electrodes), or applying a suitable bias voltage between the two electrodes, as will be discussed in more detail below. This period could be anything between a few seconds (or less) to several hours. During this time, the gas sensor may be able to consume substantially no target gas (as in the case where the sensor is open circuited), or its consumption level may be kept very low.

During this period, over time, oxygen will diffuse into the dead volume 22, and the concentration of oxygen within the dead volume will increase. This is illustrated in FIG. 4B. If left long enough, the dead volume 22 will reach equilibrium with the external concentration in the atmosphere to which the sensor is exposed.

The duration for which the sensor is able to collect gas (i.e. when little or no gas is being consumed) may be a predetermined duration in the sense of a pre-set amount of time, or the sensor may simply be left open circuit (for example) during a convenient period, e.g. overnight. It is not essential, in all cases, to know exactly for how long the predetermined duration lasts. However, in many cases this information is useful and so pre-set times may be used or the duration of gas collection may be measured as it happens. Moreover, in practice leaving the sensor open circuit for a very long time may result in oxygen dissolving in the electrolyte, which will cause a very long, slow transient as it is consumed. This could be avoided by the use of an electrolyte in which the target gas is not soluble, such as a solid electrolyte. However in other cases this mechanism could be made use of by using the technique to get a measure of the target gas's solubility/diffusion in the electrolyte.

In the next step, the ability of the sensor to consume gas is increased, preferably back to its working level. This may be immediate (e.g. closing an open circuit), or gradual (e.g. changing an applied bias voltage). A large transient signal will be observed as the sensor consumes the oxygen which has been collected in the dead volume. This is illustrated in FIG. 4C, where the arrows TR represent the consumption of gas by the electrode during the transient. Depending on the relative sizes of dead volume and capillary, this transient current may be orders of magnitude higher than the steady state diffusion limited current.

Figure 5A:
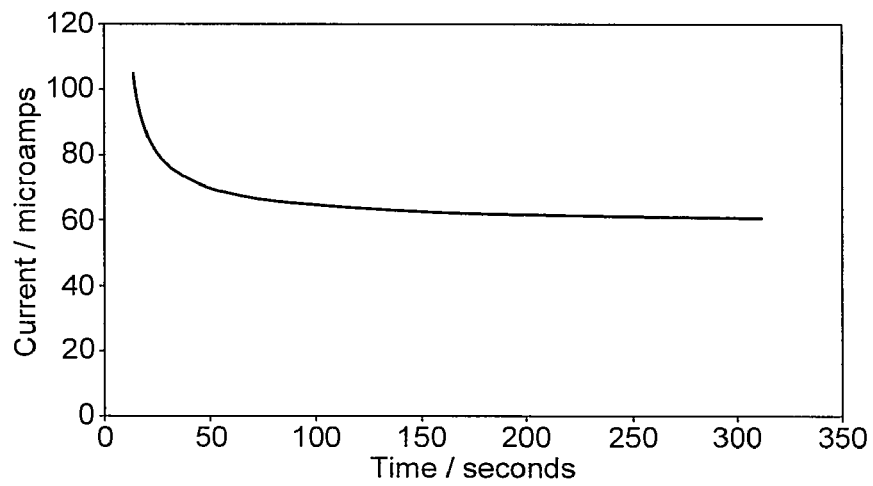
FIGS. 5 A, B and C are graphs showing exemplary sensor outputs during the steps depicted in FIGS. 4 A, B and C respectively, FIG. 5C illustrating a transient decay signal obtained in accordance with a first embodiment of the invention.
Figure 5B:
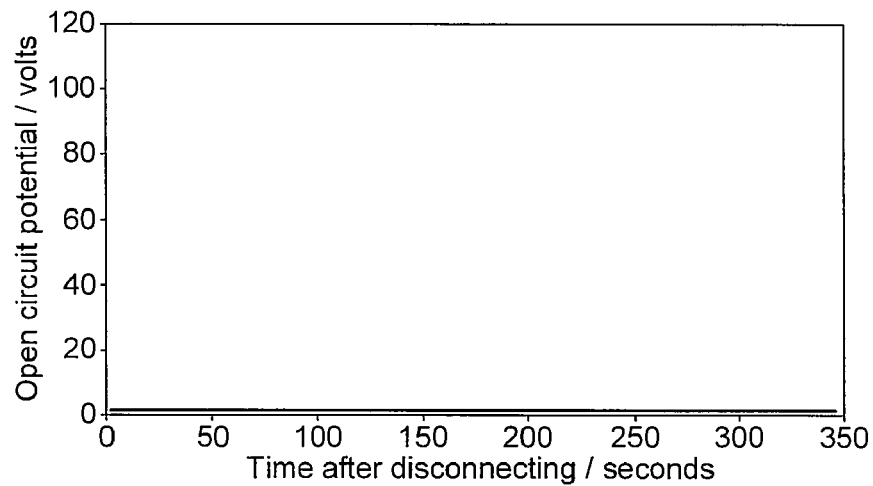
Figure 5C:
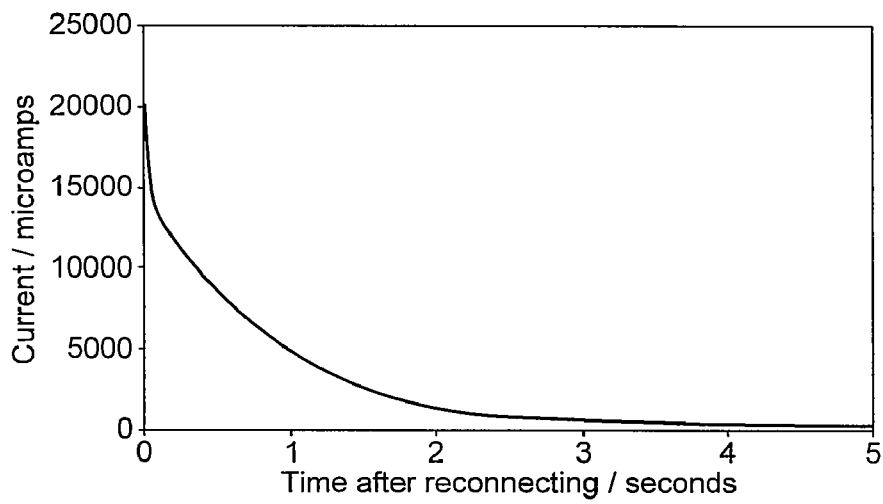

FIGS. 5 A, B and C show exemplary output signals from the sensor during each of the operational periods described above. In FIG. 5A, the sensor is operating in normal steady state mode, the level of which is directly related to the concentration of the target gas in the surrounding atmosphere (the initial transient is caused by the switch-on of the instrument and the subsequent stabilisation period is necessary in this experiment because the sensor has been off load for a short, undefined time period prior to the start of the experiment. In practice sensors would normally be on load continuously so this stabilisation period would not be necessary). In FIG. 5B, the sensor is left open circuit for around 350 seconds during which its output current is zero. FIG. 5C shows the decay transient curve when the sensor circuit is reconnected, over the first 5 seconds before the sensor returns to steady state operation. It should be noted that the axis scale of FIG. 5C covers a much greater range than those of 5A and 5B, in order to display the full transient. In this step, the current transient is recorded rapidly (e.g. every 2 milliseconds) for a period (e.g. 5 seconds) which is sufficient for the current to decay almost back to the steady state value.

As mentioned above, it should be noted that the first of these three operations, shown in FIGS. 4A and 5A, is optional and does not necessarily need to be performed before carrying out the steps shown in FIGS. 4B/5B and 4C/5C. Nonetheless it is preferable to ensure the sensor is operating in steady state mode before starting the open circuit duration to ensure there is zero oxygen concentration in the dead volume.

In some embodiments, the potential between the sensing and counter electrodes may be monitored during the open circuit phase (i.e. during the step depicted in FIG. 5B). This is discussed in more detail below.

The above operations can be carried using an essentially conventional sensing circuit, such as those shown in FIG. 2, controlled using a processor programmed appropriately, provided with:

A means of disconnecting the sensor from the load resistor, such as a relay, FET or other solid state switching device.

The ability to measure much higher currents and at a faster sampling rate (milliseconds) than may normally be required.

Optionally, a means of monitoring the open circuit potential.

Figure 6A:
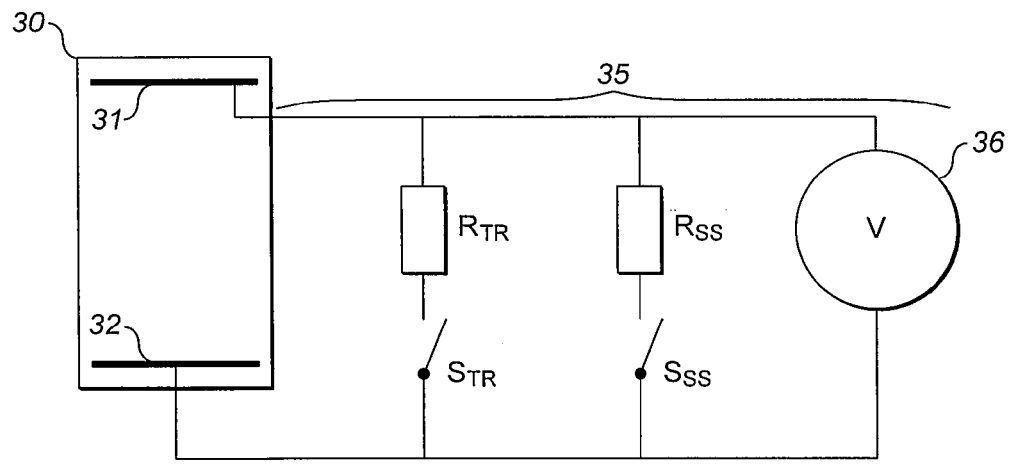
FIGS. 6 A, B and C are schematic circuit diagrams showing exemplary sensing circuits which may be used to perform embodiments of methods of controlling the operation of the gas sensor.

However, as described below, in certain embodiments of the present invention, the sensing circuit may be modified. Examples of such sensing circuits are shown in FIGS. 6 A, B and C. In each case the circuit is connected to the gas sensing electrode 31 and counter electrode 32 within schematic gas sensor 30. In FIG. 6A, the sensing circuit is provided with two load resistors $R_{SS}$ and $R_{TR}$ in parallel with a voltage meter 36. Switches $S_{SS}$ and $S_{TR}$ are provided to control which of the resistors the load is placed across, and to enable the circuit to be broken. The load resistor $R_{SS}$ is used when the sensor is operating at steady state (i.e. normal operation), whereas for at least part of the transient decay signal, a second load resistor $R_{TR}$ may be used in place of load resistor $R_{SS}$. This is because, as mentioned above, the transient current may be many orders of magnitude higher than the steady state current. As such a lower value load resistor may be preferable in order to avoid limiting the sensor current, and to reduce the voltage range which the voltage meter 36 need be able to measure. In other cases, however a high value load resistor $R_{TR}$ may be desirable and this will be discussed below in relation to the fourth embodiment. The alternative circuits shown in FIGS. 6 B and C will be described in relation to the second and third embodiments.

Figure 7:
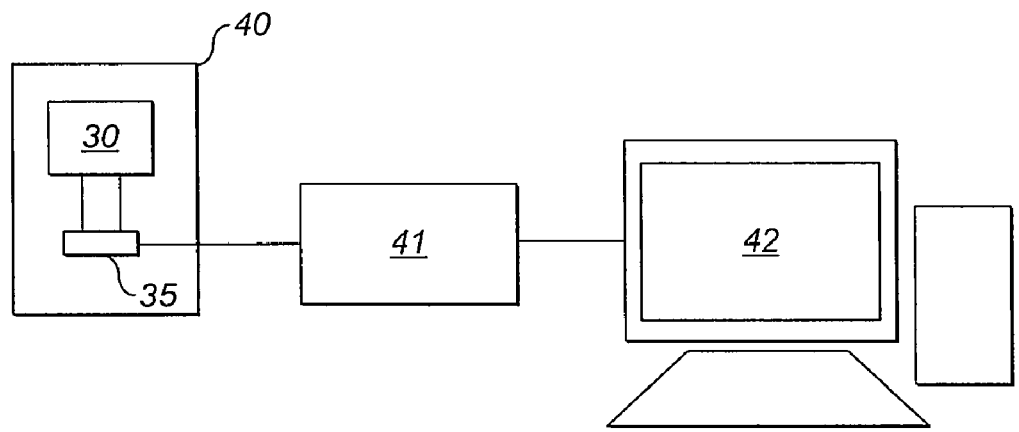
FIGS. 7 and 8 illustrate two exemplary apparatus which may be used to perform embodiments of methods of controlling the operation of the gas sensor.

Gas sensors such as that to which the present invention may be applied typically form part of a gas sensing device, which may be mounted statically at a sensing location or be designed to be carried or worn by a user. Typically such a device 40 (shown in FIGS. 7 and 8) includes, as well as the gas sensor 30, the sensing circuit 35 and, optionally, a module for outputting an alarm, such as a sounder or a light, or a display such as an LCD (not shown). The device 40 is typically battery-powered although static devices may have mains connections. To perform methods in accordance with the present invention, the gas sensor can be controlled by a processor 41 programmed accordingly. The processor 41 may be external to the sensing device 40 (as shown in FIG. 7), or could be integral to the sensing device 40 (not shown). The processor connects to the sensing circuit 35 for control thereof. The connection could be a wired or wireless connection, and could take place through a network. The processor may also be connected to a storage or output means such as computer 42 (of which the processor 41 could form part), which may be remote to the sensing device 40 and/or the processor 41. However, typically, the method would be implemented in a portable sensing instrument, with the device being connected to a computer only for occasional more sophisticated measurements, such as in house quality control or customer returns.

Figure 8:
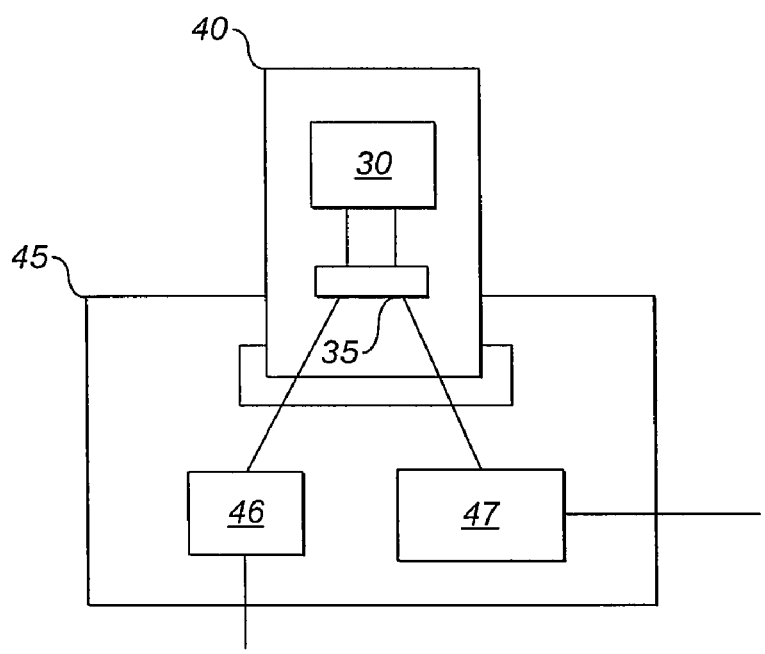

In one particularly preferred example, the processor is connected to the sensing device 40 via a docking station 45, shown in FIG. 8. Essentially, this provides a convenient electronic connection between the sensing circuit 35 and the processor, which in this example is integral with the docking station and indicated as 47. Conveniently, the housing of the docking station is arranged to hold the sensing device 40 such that it may be used for storage of the device. The processor 47 may be connected as before to a storage or output means, which may or may not be integral with the docking station. The docking station may also include recharging means 46 for recharging the battery of device 40, and therefore preferably includes a mains power supply.

In embodiments of the present invention, the decay transient signal (such as that shown in FIG. 5C) is monitored and analysed by a processor and/or computer in order to extract information about the performance of one or more components of the electrochemical gas sensor. In some cases, the extracted information may relate to a group of components, e.g. the electrode assembly, and in other cases individual components can be assessed, e.g. the gas diffusion barrier. Different forms of analysis may be performed in order to extract different information, for instance:

The rate of current decay during the transient will be a function of the catalytic activity of the electrode and/or diffusion limitation of the membrane supporting the electrode, and may also depend on factors such as bulk flow of gas into the sensor. Thus, as described in more detail below, determining the rate of decay of the transient decay curve can provide a measure of the effective 'open electrode' activity, defined as the gas response the sensor would give if it were not capillary limited. This can be used to determine whether the electrode is suffering from a fault such as lost catalytic activity, partial blocking or a reduced effective diffusion coefficient (e.g. if it is flooded with electrolyte).

The above parameter is a composite parameter (i.e. a combination of diffusion and kinetic parameters), but it is possible to further resolve such parameters into their constituents by performing more sophisticated measurements as will be described in more detail below.

During the gas collection phase, the time dependence of the build-up of oxygen in the dead volume is a function of the volume itself and the diffusional restriction of the capillary. Therefore this can give a quantitative measure of the behaviour of the capillary. This also allows the detection of a possible 'fail unsafe' failure mode due to additional gas leakage paths in parallel with the capillary (e.g. cracking of the sensor top). As described below, the rate of oxygen build-up can be determined by performing multiple measurements with different open circuit times.

The integrated charge under the subsequent measurement transient gives a direct measurement of the oxygen concentration in the dead volume, independently of any diffusional or kinetic limitations. This can then in principle be then used to calibrate the subsequent steady state gas sensitivity, especially if the open circuit phase is sufficiently long to ensure equilibration between the oxygen concentration in the dead volume with that in the surrounding atmosphere.

If the open circuit potential is measured during the open circuit period, this can provide another measure of the build up of target gas in the dead volume. The potential of the open circuit sensing electrode is a function of target gas concentration. A single open circuit measurement can be used to obtain all of the necessary information.

Examples of particular ways in which the above forms of analysis may be implemented will now be described.

Rate of Decay Analysis

As indicated above, the rate of decay (i.e. time dependency) of the transient decay curve is related to the performance of the electrode assembly—i.e. the rate of gas reaction at the sensing electrode. The shape of the transient may also be affected by factors including bulk flow into the sensor.

It should be noted that the decay curve may well not take the form of a conventional linear or exponential decay. In practice, there is an initial rapid phase of decay which is believed to be partly due to capacitative discharge and partly due to the finite diffusion coefficient of collected gas within the dead volume. The rapid capacitative discharge part of the curve can easily be removed or compensated for by performing a simple capacitative measurement such as a potential step measurement. As a result it is generally found that at short times, the output current is inversely proportional to the square root of time, as predicted by the electrochemical Cottrel equation (see for example Bard, A. J.; Faulkner, L. R. "Electrochemical Methods. Fundamentals and Applications" 2nd Ed. Wiley, New York. 2001. ISBN 0-471-04372-9), whereas at longer times the behaviour tends toward an exponential decay.

The rate of decay of the transient decay curve may be analysed in a number of ways. In a first embodiment of the present invention, the rate of decay of any one transient decay curve, such as that shown in FIG. 5C, can be used to extract information. The behaviour of the sensor can be modeled and applied to the measured decay signal in order to extract a time constant representative of the rate of decay, or one or more approximate gradients can be taken from one or more points along the decay curve. Generally speaking, the rate of decay is indicative of the electrode assembly's performance, in terms of its kinetic and diffusional performance combined. The greater the rate of decay, the better the overall performance of the electrode assembly. This may be used by itself to give a measure of the electrode assembly's performance. However, it is useful to compare the measured rate of decay with stored data representative of adequate (or conversely, inadequate) performance, to determine whether the electrode assembly is operating within acceptable limits. For example, if the measured decay curve decays more rapidly than a stored curve representing adequate performance, it can be deduced that the electrode assembly is performing well and need not be interrogated further. If the measured decay curve decays more slowly then the stored curve, the electrode assembly may be at fault and further investigation such as that described below may be performed. The measured rate of decay may alternatively or in addition be compared with a scale of stored values.

To extract more information about the performance of the electrode assembly, in second, third and fourth embodiments of the invention, the kinetic behaviour of the gas sensing electrode is varied and its effect on the rate of decay of the transient studied. This can be achieved by varying the bias voltage applied to the electrochemical gas sensor.

Normally, lead anode oxygen sensors are operated 'unbiased', meaning that the working electrode is held at the same potential as the lead anode. This gives an electrochemical activity which is usually many orders of magnitude higher than necessary—i.e. the behaviour of the sensor is limited by diffusion of gas to the electrode and the electrode is sufficiently active that it can consume all the gas which arrives at the electrode (and more). Electrochemical oxygen 'pump' sensors are typically operated with an applied bias voltage to achieve a similar behaviour. While the sensor is operating in a diffusion limited regime, variations in the activity of the electrode will not affect the rate of reaction (and so the output signal).

Figure 9:
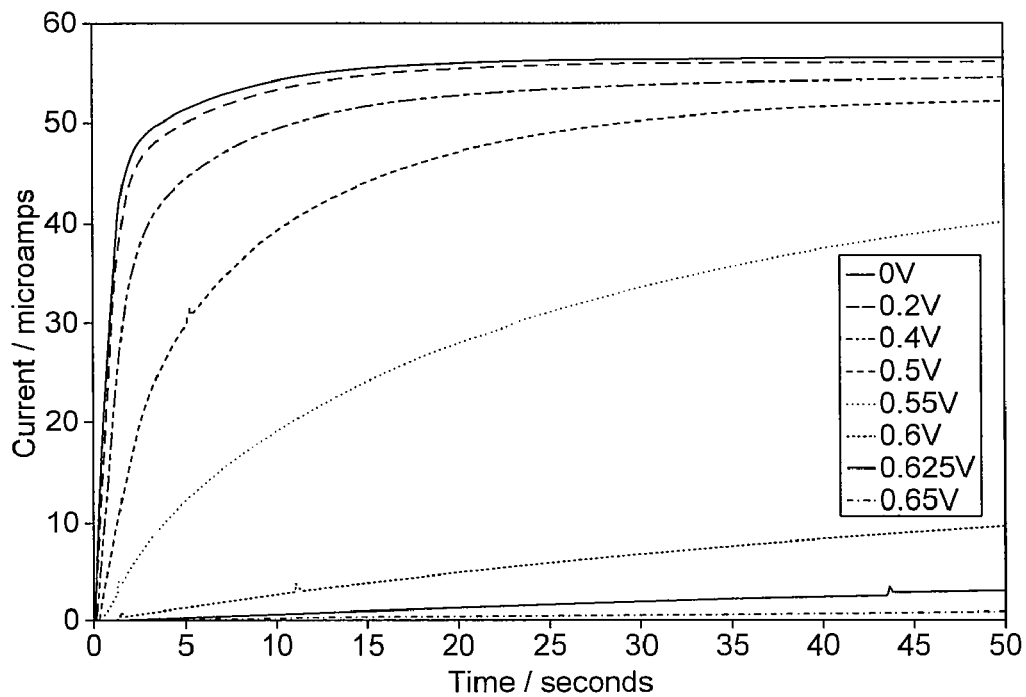
FIG. 9 is a graph showing the response of an exemplary electrochemical oxygen sensor to a change in oxygen concentration from zero to 21 vol %, as a function of applied bias voltage from 0 V (vs. a lead anode) to 0.65 V.

However, it is possible to reduce the electrode activity so that the sensor operates in a kinetically limited mode (even when fitted with a capillary) by applying a suitable bias voltage to the gas sensing electrode: in the case of a consumable lead anode sensor this may involve directly applying a bias voltage between the two electrodes for example as shown in FIG. 2a or 2b. In the case of a three electrode oxygen pump or toxic sensor, a bias potential may be controlled between the sensing and reference electrodes by adjusting the potential between the sensing and counter electrodes, for example as shown in FIG. 2c. By adjusting the bias potential towards the open circuit potential, the gas reaction can be reduced or even stopped (at the open circuit potential). To illustrate this, FIG. 9 shows the response of an exemplary oxygen sensor on being exposed to 21 vol % oxygen at time=0, at a range of bias voltages between 0V and 0.65V. It will be seen that as the applied bias voltage increases, not only the magnitude of the current, but also the speed of response of the sensor decreases rapidly.

Although the magnitude of the steady state current is only significantly affected when the bias voltage becomes large, relatively small changes in bias voltage have a significant effect on the speed of response. This is shown clearly in FIG. 10 which shows the bias voltage dependence of the steady state response and the time taken for the signal to reach 90 or 95% of its steady state value ("T90" and "T95" respectively) for an exemplary oxygen sensor. It can be seen that the response slows down significantly (by more than a factor of two) before the steady state response begins to be noticeably affected. The same is true however the activity of the sensing electrode is reduced, not necessarily by means of an applied bias voltage but also, for example, should a proportion of the electrode catalyst become poisoned, or if the effective active surface area of the working electrode is reduced, or if the electrochemical potential of the reference or counter electrode to which the sensing electrode is referenced changes. This is particularly important, since failure of a sensor by loss of electrode activity in this way could give rise to an 'unsafe' failure—i.e. the sensor may still perform normally during calibration or conventional 'bump' testing (i.e. gas testing), but its response time may be too slow to respond in a hazardous situation.

In the second embodiment of the invention, the gas sensor is operated as described above, but with the steps being repeated at least twice (in total) using different applied bias voltages. For example:

1) Allow sensor to stabilise in atmosphere at its normal operating bias (which may be zero);
2) Open circuit sensor (or apply suitable bias voltage) for predefined time (in this example 300 seconds);
3) Reconnect sensor at a first bias voltage and measure current decay transient;

4) Return to normal operating bias—this need not be the same as the bias applied in step (1);
5) Repeat (1) to (3) for at least a second (different) bias voltage in step (3).

In experiments, an open circuit time of 300 seconds was used since this gives a reasonably large and measurable transient. In practice, a longer or shorter time may be used, or it may be beneficial to use a range of open circuit times and bias voltages. Further, it is not essential that the exact duration of the "open circuit" time is known, although it is preferable that this is kept constant in each repetition of the steps.

In this example, the sensor is re-equilibrated at zero volts bias (steps 1 and 4) between each transient measurement at different bias voltages, to ensure that all of the collected oxygen is purged before each open circuit period. This may not be necessary.

Figure 11:
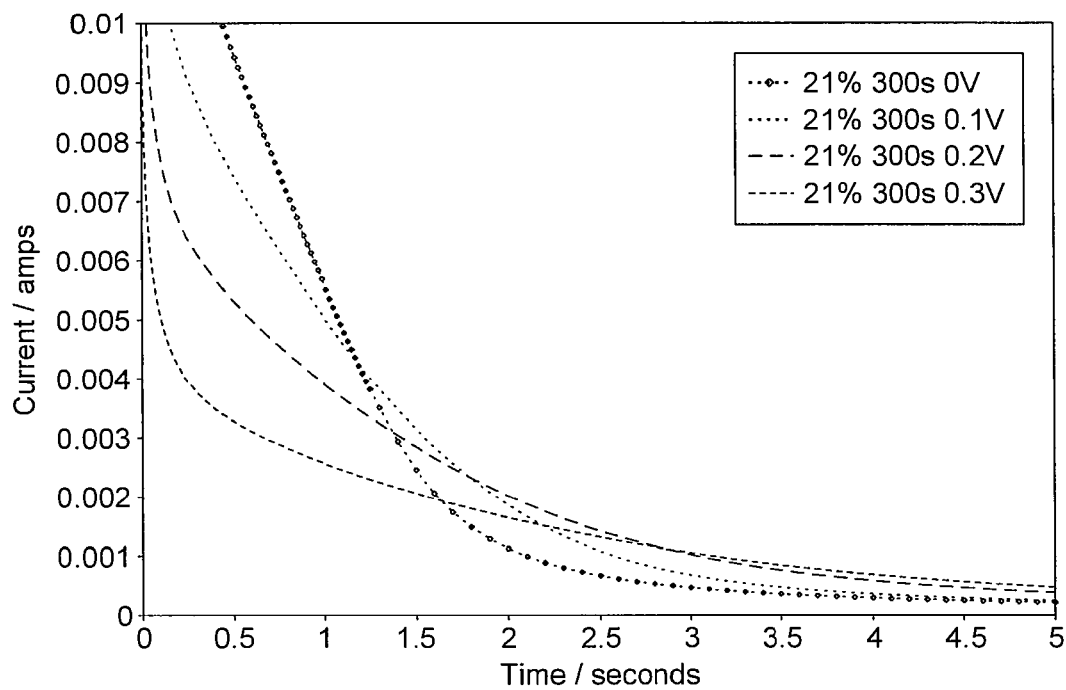
FIG. 11 is a graph showing the transient decay curve of an exemplary oxygen sensor at varying applied bias voltages, where the sensor has been exposed to air for 300 s open circuit time, in accordance with a second embodiment of the present invention.

The resulting decay curves give a measure of the dependency of the rate of decay on the applied bias voltage: FIG. 11 shows the effect of bias voltage on the decay transient for a sensor which is operating (or has been forced into) a kinetically limited regime. It is clear that increasing the bias voltage (decreasing electrode activity) results in a slower rate of current decay—i.e. a slower rate of oxygen consumption. At lower bias voltages (i.e. voltages closer to the sensor's normal operating bias) the initial transient current is higher due to the faster rate of oxygen consumption. The rate at which the current decays is also faster, for the same reason. For example it can be seen from FIG. 11 that the current at zero volts bias starts off much higher than at the higher bias voltages, but the current rapidly drops below the currents for the higher bias voltages. The total integrated charge under each curve should ideally be equal, however some small deviations occur—for example due to additional gas being 'sucked' into the sensor due to the reduced pressure cause by rapid oxygen consumption, or due to diffusion of gas into or out of the diffusion limiting capillary or membrane over longer time scales.

By analysing how the rate of decay changes with applied bias voltage, the second embodiment can provide information as to the kinetic performance of the gas sensing electrode. In a "healthy" sensor, with significant excess activity reserve, for small variations from the normal operating bias voltage, there should be no change to the rate of decay observed (unlike the scenario shown in FIG. 11). The embodiment can therefore be used to determine whether a sensor has sufficient activity reserve by comparing the rates of decay across a predetermined range of applied bias voltages for which a "healthy" sensor would be expected to stay within the diffusion limited regime. If no change to the rate of decay is observed, the electrode assembly can be deemed to be performing well, whereas if a change is observed, it can be deduced that the gas sensing electrode's activity is low.

As an extension, decay curves could be obtained over a range of bias voltages which would be expected to take even a healthy sensor out of its diffusion limited regime, in order to determine at approximately what level of applied bias voltage the regime change occurs. For example, decay curves could be obtained at a number of applied voltages from the normal operating bias up to the open circuit voltage, the lowest applied voltage at which a change is observed providing an indication of the "health" of the gas sensing electrode. The greater the difference between this voltage and the normal operating bias voltage (if any), the greater the level of activity reserve.

Since even a small change in applied bias voltage gives a large change in the rate of decay of the decay transient (when the sensor is in the kinetically limited regime), this technique is much more sensitive to changes in the electrode's activity than any based on the magnitude of the steady state signal.

Figure 10:
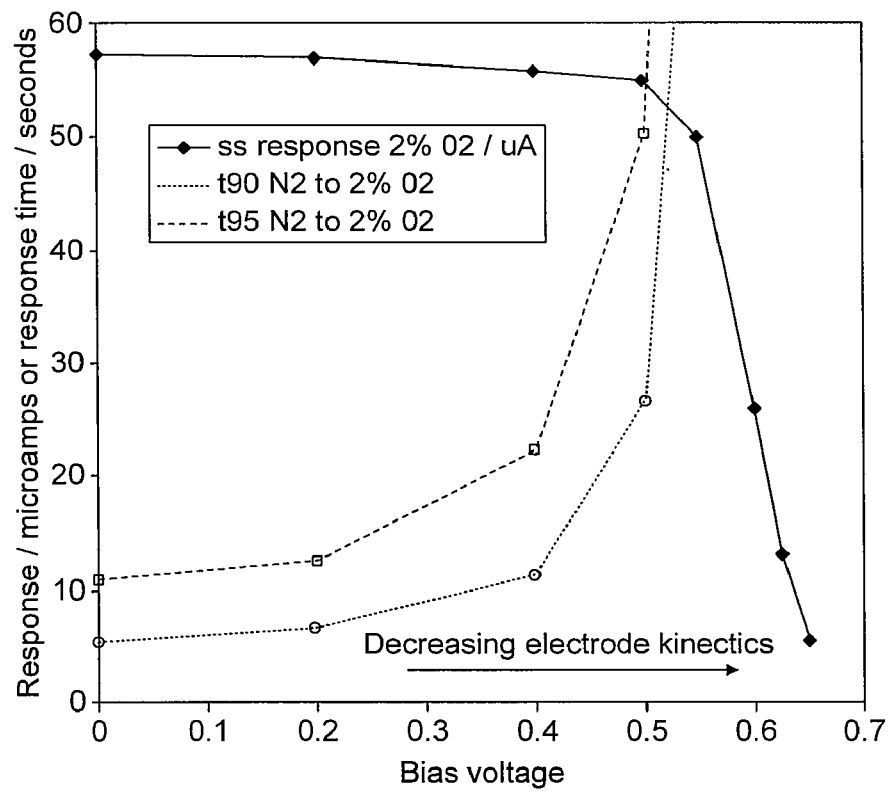
FIG. 10 is a graph showing the dependence of the steady state response of an exemplary electrochemical oxygen sensor at 21 vol % oxygen on applied bias voltage, and the dependence of the electrochemical oxygen sensor's rate of response, expressed as the time taken to reach 90% and 95% of the steady state value ("T90" and "T95" respectively), on applied bias voltage.

This is demonstrated by the behaviour illustrated in FIG. 9 and FIG. 10, which show that much larger bias voltages are required before significant effects are observed on the steady state response. The technique can therefore act as an 'early warning' that electrode activity is changing, long before the effects actually become an issue.

Hence, the results of this analysis provide an indication as to whether the gas sensing electrode has become kinetically limited. If not, and the performance of the electrode assembly has been determined not to be acceptable (using the technique of the first embodiment), then it can be deduced that the electrode is suffering a diffusive limitation, such as flooding of the electrode membrane.

In third and fourth embodiments of the present invention, the dependency of the rate of decay on bias voltage is analysed based on the same principles as already described. However, rather than repeat the cycle of steps at a range of different bias voltages, in the third embodiment, the applied bias voltage is varied during the decay transient. Hence, the same information as deduced in the second embodiment can be extracted from a single transient decay curve.

Figure 12:
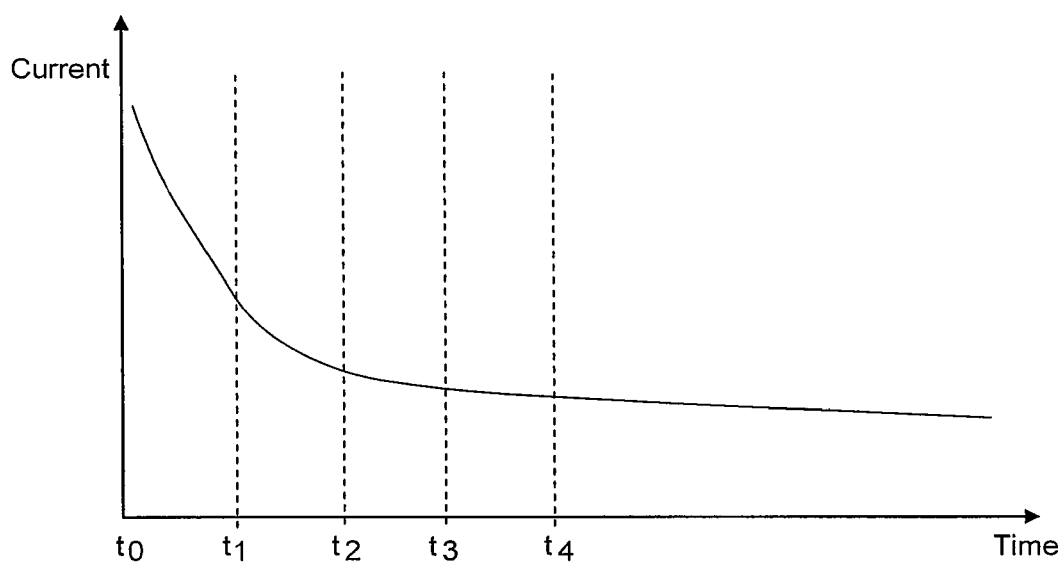
FIG. 12 is a schematic graph showing the transient decay curve of an exemplary electrochemical gas sensor operated in accordance with a third embodiment of the invention.

An example of a decay transient curve produced in accordance with the third embodiment is shown in FIG. 12. Here, the "open circuit" period ends at time=$t_0$ and between $t_0$ and $t_1$, a first bias voltage is applied. At $t_2$, the bias voltage is adjusted, and again at $t_3$ and $t_4$. A minimum of two different bias voltages is required although the greater the number of different values, the more accurate the result (as in the case of the second embodiment). The rate of decay is determined for at least two regions of the decay curve, where the applied bias voltage is different in each of the at least two regions. For example, the rate of decay might be determined between $t_0$ and $t_1$, and then between $t_1$ and $t_2$. Preferably the rate of decay is determined for each of the different applied bias voltages.

As in the case of the second embodiment, the rate of decay at one bias voltage is compared with that at another bias voltage to determine whether the gas sensing electrode is operating in a diffusion limited mode (if there is no change in the rate of decay), or in a kinetically limited mode. The technique can also be used to estimate the voltage at which the electrode switches between regimes to give a measure of its "health", as before. Using this approach only a single transient measurement is needed to obtain and discriminate kinetic and diffusional information, although in practice more than one such measurement may still be taken.

Figure 6B:
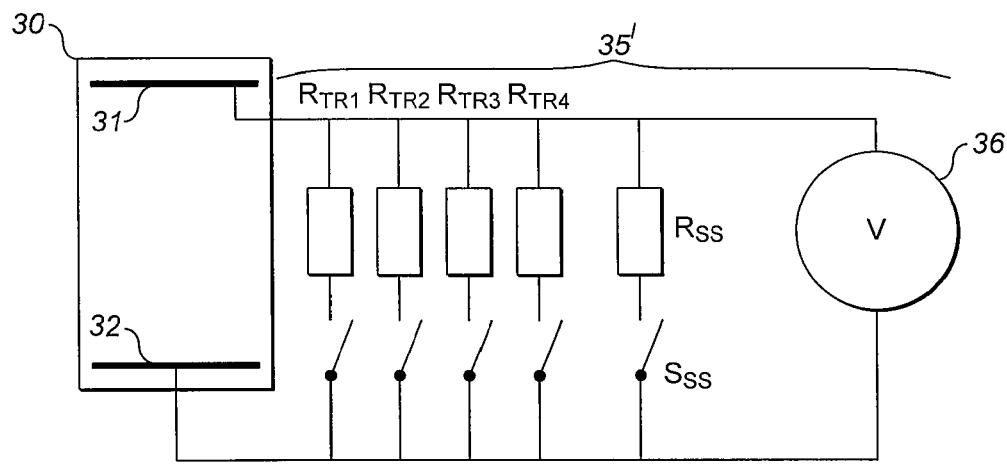

To control the applied bias voltage in the second or third embodiments, a conventional two electrode potentiostat or current follower type approach (as shown in FIG. 2B but where $R_{load}$ is low or omitted) can be used, with the ability to vary the applied voltage under the control of a processor. Alternatively, sensing circuits such as those shown in FIGS. 6 B and C could be used. In FIG. 6B, a plurality of load resistors $R_{TR1}$, $R_{TR2}$, $R_{TR3}$ and $R_{TR4}$ of different values are provided in parallel with a voltage meter 36 and (optionally) another load resistor $R_{SS}$ for use in steady state operation. In practice, one of the "transient" load resistors could be used for this. Corresponding switches (controlled by the processor) are provided such that any of the resistors can be switched in or out. In the second embodiment, the load from the sensor 30 is switched between different resistors (or combinations thereof) between obtaining each decay curve. In the third embodiment, different resistors are switched in during one decay curve.

Figure 6C:
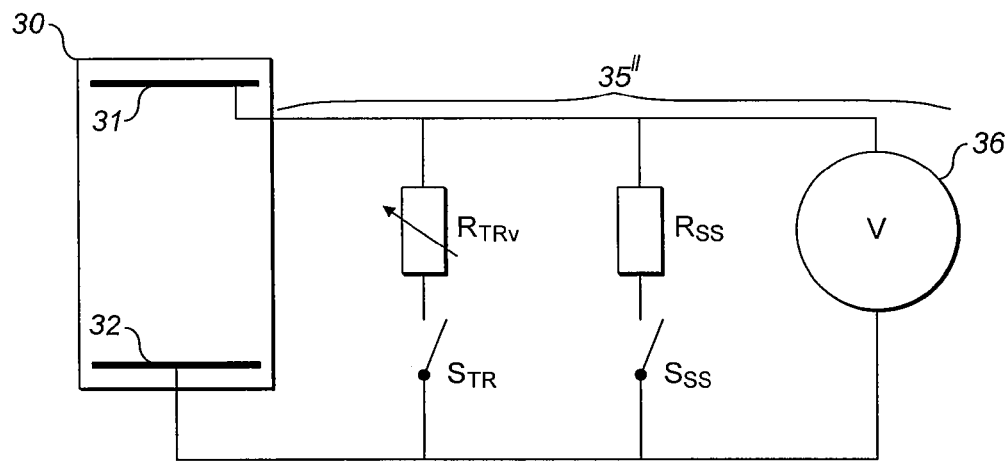

In a further alternative, an actively adjustable, variable-resistance load resistor $R_{TRv}$ could be used instead, as shown in FIG. 6C. Again, the separate steady state load resistor $R_{SS}$ is optional. The variable resistance load resistor could comprise a transistor or a solid state potentiometer, and the variable resistance $R_{TRv}$ and switch $S_{TR}$ may be combined into a single component. Such a device could either be preset to a particular resistance (or I/V characteristic value) or could actively be adjusted in a form of potentiostat circuit to maintain a constant or varying bias as required.

Figure 13:
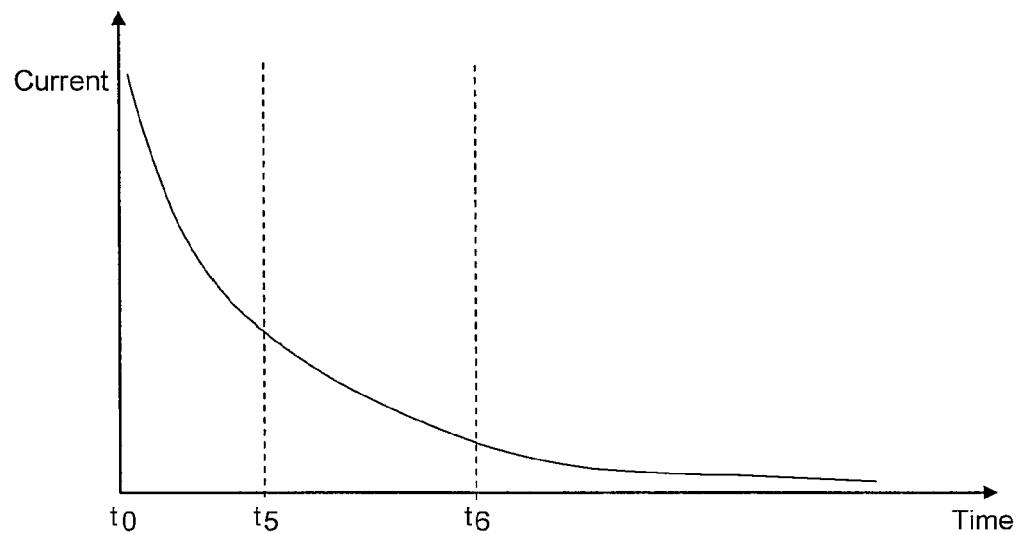
FIG. 13 is a schematic graph showing the transient decay curve of an exemplary electrochemical gas sensor operated in accordance with a fourth embodiment of the invention.

In a fourth embodiment, the bias voltage is allowed to vary as a function of the circuit current, during one decay curve. An exemplary decay curve is shown in FIG. 13. This can be achieved by using a relatively high value load resistor $R_{TR}$ (in the circuits of FIG. 2B or 6A, for example) so that the bias voltage (generated across the load resistor) starts off high when the transient current is high, then as the current decays the bias voltage decreases in proportion. For example, if the load resistor is 10 ohms, then with an initial transient of 20 mA the sensor is effectively biased to 200 mV. The bias voltage then decreases towards zero over time. The electrode kinetics would then be increasing with time during the transient, and the gradient of the transient (rate of oxygen consumption) would change over time (where the sensor is operating in a kinetically limited regime). The rate of decay of the curve can be determined for at least two positions along the curve, such as $t_5$ and $t_6$ in FIG. 13, at which the applied bias voltage differs. The information can be used in the same manner as in the case of the third embodiment.

Figure 14:
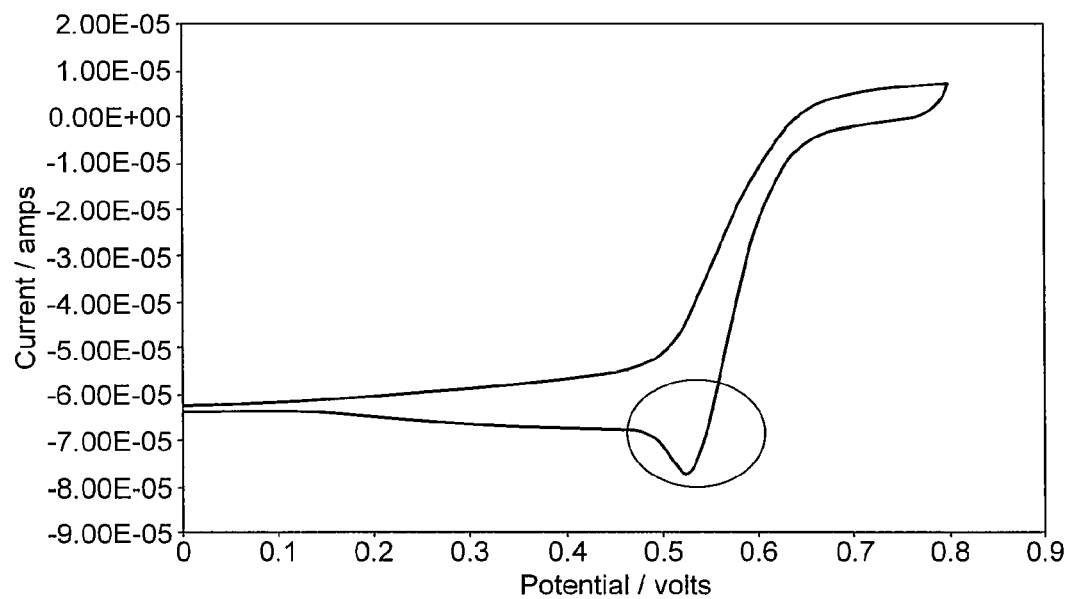
FIG. 14 is a graph showing the variation of signal current with applied bias voltage for an exemplary electrochemical gas sensor operated in accordance with a fifth embodiment of the invention.

In a fifth embodiment, similar measurements to those described above can be achieved by performing a cyclic voltammetry measurement. FIG. 14 shows the behaviour where the potential across the sensor is swept linearly from its normal value (0V) to its open circuit potential (+0.8V) and back. In the example shown, each scan takes 1 hour. On the forward scan the current drops away as the electrode reaction rate decreases. Oxygen will then build up in the dead volume. On the reverse scan, as the electrode reaction increases there is an overshoot in current (circled), due to consumption of the oxygen in the dead volume. The "sharpness" of the peak gives a measure of the rate of oxygen consumption.

Since the change in potential (and therefore reaction capability of the electrode) is gradual, the open circuit time may be defined as the duration for which the bias voltage is within a certain range, which may include the open circuit potential. For example, in the experiment of FIG. 14, the "open circuit" duration could be defined as the duration for which the bias voltage is between around 0.6 and 0.8 V. It can be seen from the Figure that the current is significantly reduced throughout this period of the cycle. In this example, the bias potential is continuously varied, but in other cases the potential could be held at the open circuit potential, for example, for a period of time. The transient decay signal would then be monitored once the bias potential returns to an "active" level which again can be defined as a range of bias voltages. Typically the ends of the first and second ranges would be equal, or at least very close, although this need not be the case if the voltage can be adjusted quickly between them.

Although this approach can give similar information to the open circuit approach, it may be less desirable for several reasons:
1) The 'open circuit' time is ill-defined as the electrode reaction is not simply 'turned off' for a specified time, but gradually decreases and increases, hence it is necessary to take into consideration the variation of the rate of oxygen consumption with bias voltage.
2) Integration of the oxygen peak requires subtraction of a varying background current.
3) Measurement of the rate of consumption (sharpness of peak) is more complicated.
4) The electronics required is more complex than for a simple open circuit measurement.
5) The sensor is actively 'driven' to voltages other than its normal operating bias, which can adversely affect it.

These factors aside, this type of approach may still be appropriate especially if the ability to scan the potential is already present in the instrument.

This approach could be used in conjunction with an empirical or theoretical model (such as a finite difference model) of the cyclic voltammetry of the sensor, fitted to the desired experimental parameters. By fitting the measured cyclic voltammogram to the model, the rate of oxygen consumption can be determined for different voltages. Such a model could readily be implemented using relatively low cost processors as used in sensing instrumentation.

One method of avoiding issue (5) above could be to open circuit the sensor for a specified time, measure its open circuit voltage and then potentiostatically ramp the voltage back down in a controlled manner.

One possible advantage of the cyclic voltammetry approach over the 'open circuit' method is that the transient current is much lower and may be easier to measure.

Another method of obtaining similar information is to perform a very slow modulation (e.g. sinusoidal) of the electrode potential and analyse the magnitude, phase and/or harmonics of the resulting signal. This differs from conventional AC impedance techniques in that the modulation potential is conventionally kept small (typically not more than 10 mV) so as not to disturb the electrode kinetics. In contrast, here, the intention would be to use a sufficiently large modulation potential (hundreds of millivolts) so that the kinetics are significantly modulated.

It will be apparent to those skilled in the art that various other techniques can be used to obtain similar information—the fundamental requirement being that the electrode kinetics are significantly perturbed, and the resulting transient effect due to oxygen build-up is interrogated.

One factor that should be considered in any of the above embodiments where the sensor is a two-electrode consumable anode sensor is that, even if the working electrode is held at a fixed bias voltage relative to the anode, the electrochemical potential of the anode may itself vary especially under the high transient currents observed. This effect should ideally be taken into account in any model of the system. This effect may be overcome by using a three electrode sensor with reference electrode (which may be a pseudo-reference perhaps also made of lead), akin to the circuit shown in FIG. 2C. Alternatively the effect can be incorporated into a "pass/fail" diagnostic since degradation of the lead anode over time is also likely to result in a different IN characteristic. This issue is of less concern in sensors such as oxygen pumps which are typically three-electrode potentiostatically controlled devices.

In summary, using the techniques of the first embodiment, it is possible to separate out the behaviour of the capillary from that of the combined underlying electrode reaction and membrane diffusion limitation. Performing the measurements of the second, third, or fourth embodiments at different bias voltages has the added benefit of allowing the effects of electrode kinetics to be separated out from membrane diffusion limitation. This makes it possible to be able to measure the electrode activity even when it is in excess, facilitating:
1) 100% sensor testing, or sample testing, during manufacture to ensure that sufficient 'electrode activity reserve' is available.
2) Detection and/or distinguishing between faults caused by internal diffusional restriction (e.g. electrode flooding, membrane flooding) and caused by electrochemical effects (electrode poisoning, shift in electrochemical potential etc).

3) Early warning of faults due to loss of activity over time—long before the loss of activity actually becomes an issue—and prediction of remaining lifetime.

4) Determining that there is still sufficient activity reserve for the sensor to operate correctly if the activity were to fall—for example if the temperature was reduced.

Finally, analysis of the rate of decay of the transient can also be used to deduce information about bulk flow of gas into the sensor. During the current transient, there is a significant reduction in pressure within the dead volume resulting in increased drive for bulk flow of gas into the sensor. If such bulk flow is not restricted, this will result in an additional transient current, complicating the shape of the decay transient. Many electrochemical gas sensors such as that shown in FIG. 1 include a bulk flow membrane (item 6) which is fitted above the dead volume, either inboard or outboard of the diffusion barrier, and which is specifically intended to reduce bulk flow of gas under conditions of pressure or temperature transients.

Figure 15:
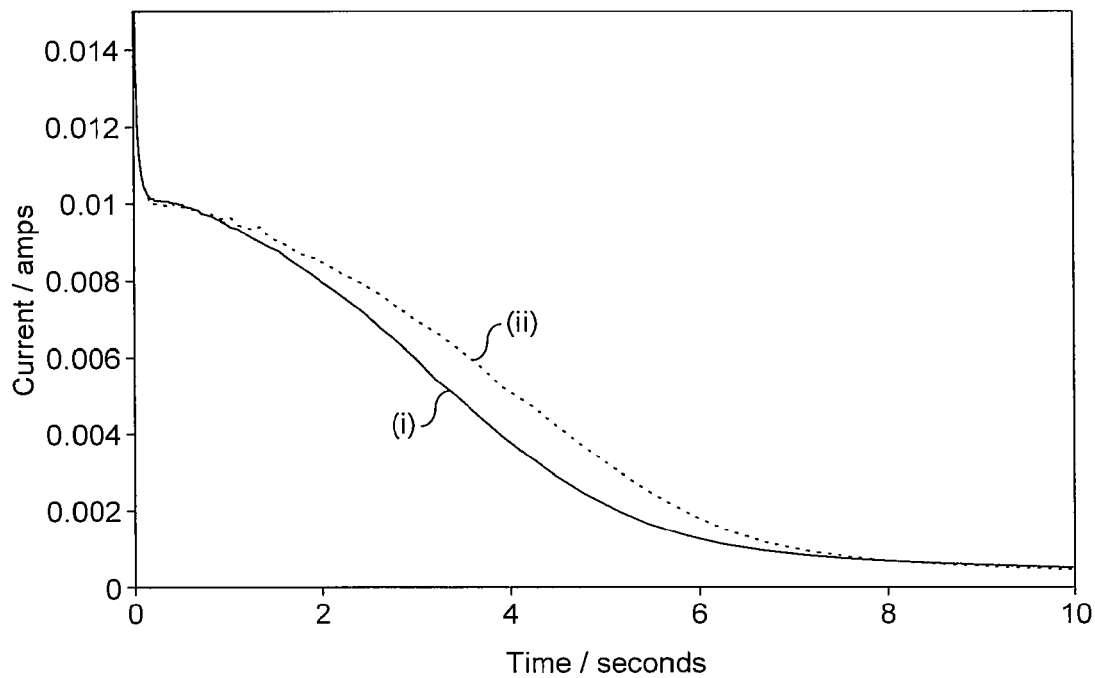
FIG. 15 is a graph showing transient decay curves for an exemplary electrochemical gas sensor (i) without a bulk flow membrane, and (ii) with a bulk flow membrane, obtained in accordance with a sixth embodiment of the invention.

By looking at the shape of the decay transient, in a sixth embodiment of the invention, it can therefore be deduced whether the bulk flow membrane is performing adequately. FIG. 15 shows decay curves for an exemplary electrochemical gas sensor and illustrates the difference in shape caused by the presence of a working bulk flow membrane. Curve (i) is for a sensor in which there is either no bulk flow membrane or a faulty bulk flow membrane is present. Curve (ii) shows the impact of a working bulk flow membrane. Therefore, in the sixth embodiment of the invention, the measured decay curve is compared with stored curves to determine whether or not a bulk flow membrane is performing adequately.

Dead Volume Filling Analysis

Figure 16:
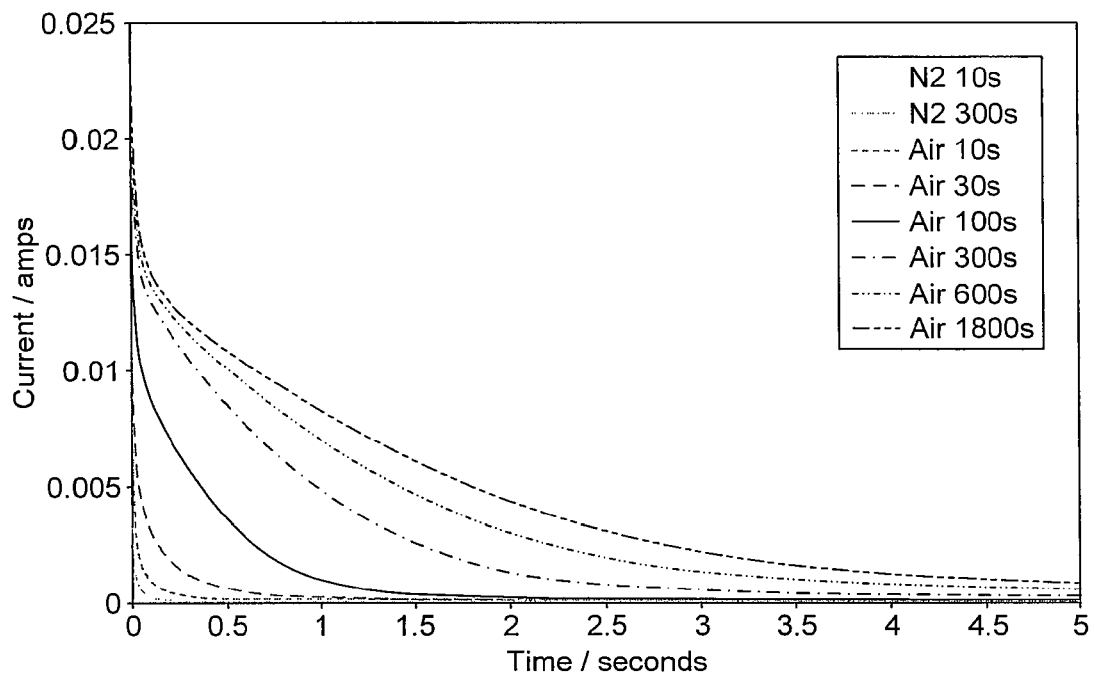
FIG. 16 is a graph showing transient decay curves for an exemplary electrochemical gas sensor operated in accordance with a seventh embodiment of the invention, for different open circuit times.
Figure 17:
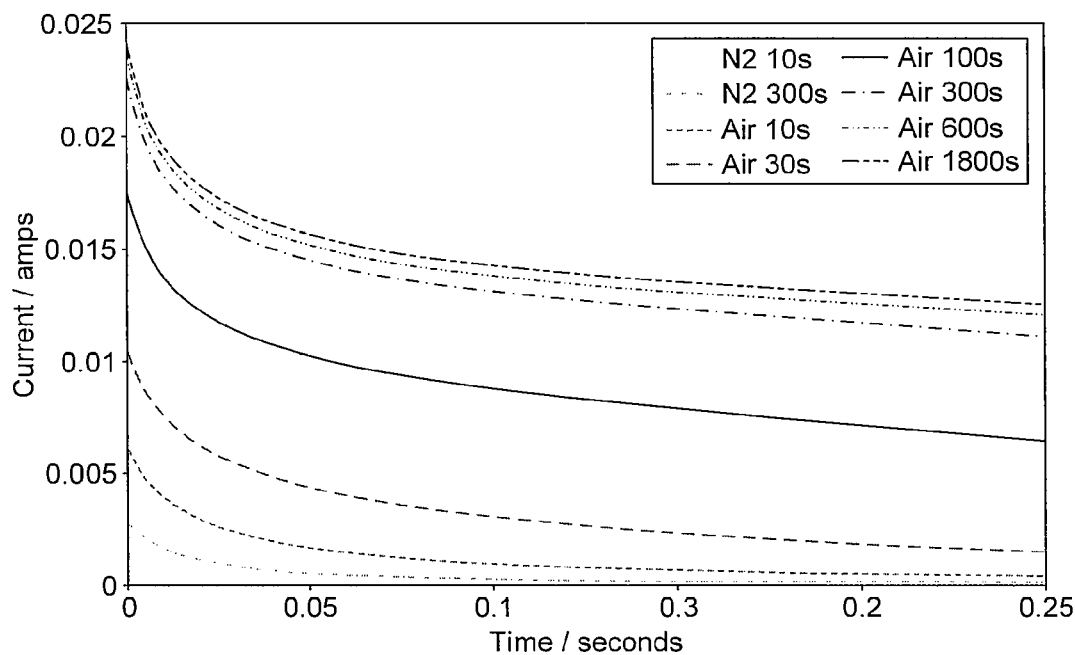
FIG. 17 is a graph showing the transient decay curves of FIG. 16 on an expanded time axis to show the early portion of the transient decay signals in detail.

The area under the decay transient can give a direct measure of the number of moles of oxygen (or other target gas) in the cavity between the electrode and capillary. FIG. 16 shows a number of decay curves, obtained for different "open circuit" times (i.e. the duration for which gas is collected while the reaction capability of the sensor is reduced). FIG. 17 shows the same decay curves on an expanded time axis to show the initial transients in more detail. It can be seen that the area under the curve increases as the open circuit time increases.

In a seventh embodiment of the present invention, this dependence on open circuit time is used to extract information about diffusional gas access to the sensor interior, i.e. the gas diffusion barrier. It should be noted that such analysis is independent of any bulk flow membrane, discussed in the sixth embodiment, since a bulk flow membrane is typically designed not to significantly affect diffusional gas access to the sensor.

In the seventh embodiment, the previously-described cycle of open-circuiting the sensor (or otherwise reducing its reaction capability) and then monitoring the resulting transient decay curve is repeated (at least twice in total) for different "open circuit" times. The total integrated area under each curve is plotted against open circuit time in FIG. 18. It can be seen that there is an initial linear increase in charge with time, which then asymptotically approaches a constant value at long times. This can be understood as the oxygen concentration within the dead volume is almost zero at low open circuit times, so the concentration gradient and hence flux of oxygen down the capillary is directly proportional to the applied oxygen concentration. As the oxygen concentration builds up, so the flux of oxygen decreases towards zero as the equilibrium is approached. Eventually the oxygen concentration inside the dead volume will equilibrate with that outside.

This data can be used in a number of ways. The time dependence of oxygen filling through the capillary is a function of the capillary volume and the rate of diffusion through the capillary. The flux, J, of oxygen down the capillary is given by:

$$J = D\frac{dC}{dx} = \frac{D}{l_c}(C_\infty - C_v) \quad (1)$$

where D is the diffusion coefficient of oxygen, $l_c$ is the length of the capillary; $C_\infty$ and $C_v$ are the oxygen concentrations (moles m$^{-3}$) in the outside air and inside the dead volume respectively. The rate of change of concentration, $C_v$, in the dead volume with open circuit time, $t_{oc}$, is therefore:

$$\frac{dC_v}{dt_{oc}} = \frac{DA_c}{l_c V_v}(C_\infty - C_v) \quad (2)$$

where $A_c$ is the cross sectional area of the capillary and $V_v$ is the dead volume. At short open circuit times, where $C_v \rightarrow 0$, equation (2) simplifies to:

$$\left.\frac{dC_v}{dt_{oc}}\right|_{t=0} = \frac{DA_c}{l_c V_v}C_\infty \quad (3)$$

Substitution of $Q_v$ for $C_v$ using Faraday's law Q=nFCV gives:

$$\left.\frac{dQ_v}{dt_{oc}}\right|_{t=0} = \frac{nFDA_c}{l_c}C_\infty \quad (4)$$

Where n is the number of electrons involved in the electrode reaction (4 for an oxygen sensor) and F is the Faraday constant (96485 A S mol$^{-1}$). This is the same as the expression giving the capillary limited ideal steady state current, $I_{CL}$. Therefore measuring the initial gradient of the plot of FIG. 18 (labeled IG) gives a direct measure of what the ideal steady state current should be for that particular sensor. If the actual steady state current observed is found to be below this value, it can be deduced that the capillary is not the rate limiting factor, i.e. the current is limited by another factor such as the electrode kinetics or diffusion limitation of the electrolyte, electrode or its supporting membrane(s). As described above, subsequent discrimination between kinetic or diffusive limitation of the electrode structure can be performed by repeating the process at different bias voltages.

This approach is advantageous since only a small number of curves at short open circuit times need be obtained—in fact, a single curve can be used if it is assumed the charge $Q_v$ at t=0 is 0 (effectively, one of the cycles used to obtain the decay curve uses an open circuit time of zero). However it is preferable to obtain a plurality of curves to improve the accuracy of the measurement.

Further, in practice it may be found that the intercept of the graph (FIG. 18), i.e. the charge seen at zero open circuit time, may not in fact be zero as expected. If so, this indicates that the electrode is not able to consume gas sufficiently rapidly, resulting in excess gas within the dead volume. This in itself is a useful indicator that the sensor is not under diffusion control.

If sufficient time is available, further information may be obtained by increasing the range of open circuit times to very long times, sufficient for the dead volume within the sensor to equilibrate with the surrounding atmosphere. Integrating equation (2), above, and using the limit $C_v=0$ at $t=0$, gives:

$$\frac{C_v}{C_\infty} = 1 - \exp\left(-t_{oc}\frac{DA_c}{l_c V_v}\right) \quad (5)$$

which is also equal to the relative charge ($Q_v/Q_\infty$) since concentration and charge are directly proportional to one another (Faraday's law).

Rearranging:

$$Q_\infty - Q_v = Q_\infty \exp\left(-t_{oc}\frac{DA_c}{l_c V_v}\right) \quad (6)$$

Figure 19:
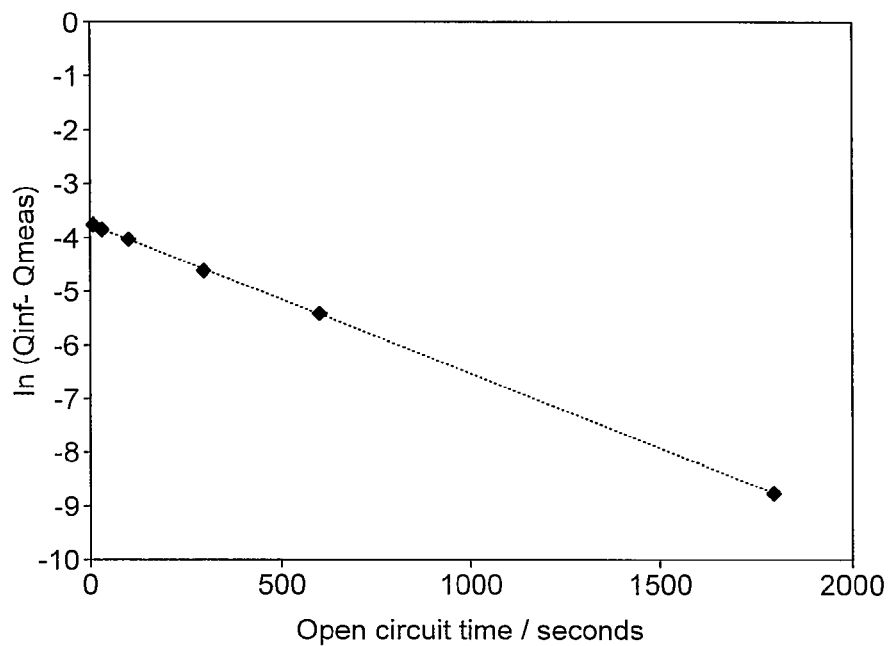
FIG. 19 shows the data from FIG. 18 as a plot of logarithm of the difference between the predicted charge corresponding to infinite open circuit time and the measured charge at each specific open circuit time, as a function of open circuit time.

Thus a plot of $\ln(Q_\infty - Q_v)$ vs open circuit time, $t_{OC}$, will be linear with gradient of $(-DA_c)/(l_c V_v)$ and intercept of $\ln(Q_\infty)$. This is shown in FIG. 19. This also shows that it is not essential to perform measurements at extremely long open circuit times in order to measure $Q_\infty$, as it is possible to extrapolate to the theoretical behaviour at infinite time. It is also not desirable to leave the sensor open circuit for extremely long times as this allows the target gas to dissolve in the electrolyte, resulting in a very long slow transient on reconnection which, although potentially useful as an additional diagnostic of oxygen diffusion in the electrolyte, results in a long delay before the sensor becomes usable. However, for sensors with electrolytes in which the target gas is not soluble, for example some forms of solid electrolyte, this may not be an issue.

The ideal theoretical capillary limited current, $I_{CL}$, is given by:

$$I_{CL} = \frac{nFADC_\infty}{l} = \frac{DA_c}{V_v l_c}Q_\infty \quad (7)$$

Therefore the gradient and intercept of FIG. 19 allow the theoretical capillary limited current to be calculated without requiring knowledge of any other parameters. Thus the actual steady state current can be compared with the theoretical capillary limited current, even if the oxygen concentration is not known (provided that oxygen is present). The data in FIG. 19 gives a value of 65.7 uA for the theoretical capillary limited current, and this is only slightly higher than the actual steady state current (60 uA), showing that in this case the sensor current is predominantly capillary limited.

It is also possible to determine the applied oxygen concentration $C_\infty$ from the intercept ($=\ln Q_\infty$) using Faraday's law, $Q_\infty = nFC_\infty V$, if the dead volume, $V_v$, is known, since n and F are known constants. This independent absolute measure of external target gas concentration can be used in conjunction with either the measured steady state current of the sensor or the integrated transient information to determine whether the diffusion limitation factor of the diffusion limiter is at its correct value—e.g. in the case of a capillary, that its effective diameter is as intended. This can be achieved using equation 7 above and the determined absolute values of $Q_\infty$ and $C_\infty$ with the known volume V to calculate the value of (D*A/l), which is effectively the diffusion limiting factor which determines the sensor current.

The ability to independently measure the applied oxygen concentration using this approach also allows self-calibration of the sensor to be performed in the field.

Alternatively, if the oxygen concentration is known, then $V_v$ can be directly calculated from the intercept, again using Faraday's law. The latter method can be used during sensor manufacture to provide a value for $V_v$ both as a quality control check and for subsequent use.

The methods of the seventh embodiment can be carried out using any of the apparatus disclosed above.

Open Circuit Potential

Figure 20:
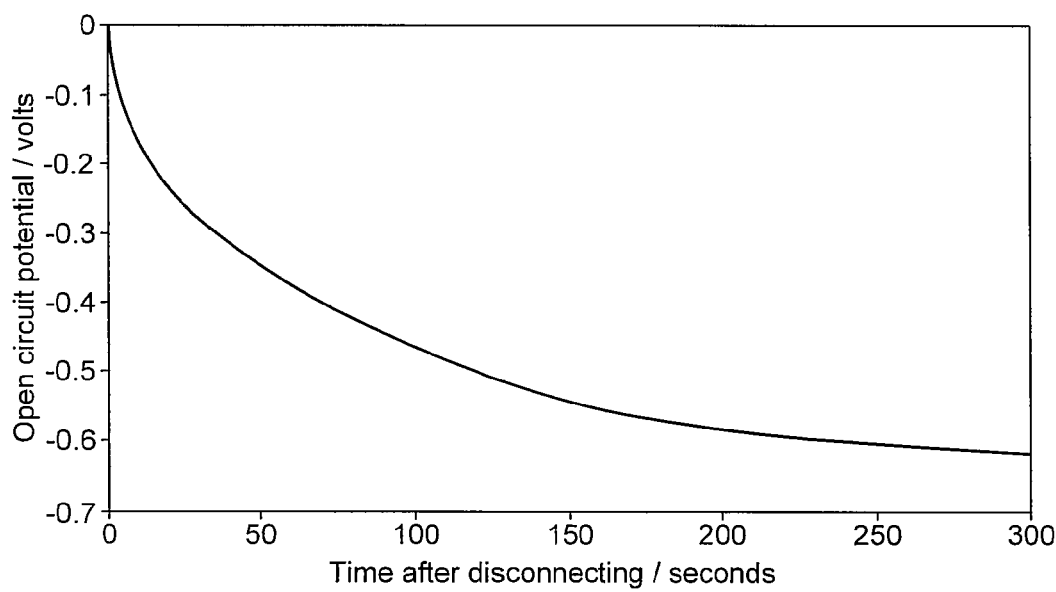
FIG. 20 is a graph showing the open circuit voltage, measured during the step depicted in FIGS. 4B and 5B, for an exemplary sensor.

In an eighth embodiment, during the open circuit (or reduced activity) period, the open circuit potential of the sensing electrode can be monitored, for example by using the sensor in a potentiometric mode. FIG. 20 is a plot of open circuit potential vs. time (where the open circuit period begins at $t=0$), and shows an example of the response which is expected to be seen.

The open circuit potential is dependent on the oxygen concentration and so increases in magnitude over time (note the y-axis scale of FIG. 20 is negative), as the gas builds up inside the sensor. Analysis of this curve can therefore provide information similar to that obtained from FIG. 18, and can be used to determine whether the diffusion barrier is performing adequately.

Figure 18:
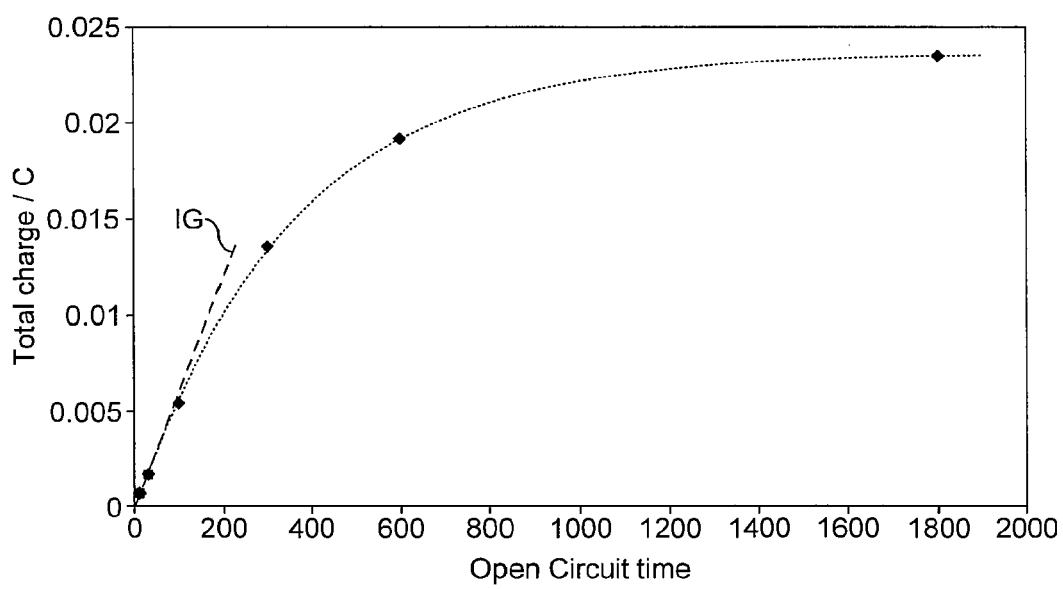
FIG. 18 is a graph showing the total charge, corresponding to amount of gas consumed, and its dependence on open circuit time, for the transient decay signals of FIGS. 16 and 17.

In principle one can obtain similar information from monitoring the open circuit potential to that obtained by performing integration of current transient measurements at multiple open circuit times, as can be seen from the similarity between FIGS. 18 and 20. The open circuit potential is a measure of the oxygen concentration in the region of the electrode, as is the integrated current transient, so it is possible to obtain information about the rate of filling of the dead volume by monitoring the open circuit potential over a single, relatively long open circuit time, without needing to measure any current transients. However the open circuit potential is also affected by other factors such as temperature, so is a less accurate or reliable measure, and is not an absolute measurement. This error may however be reduced by combining the open circuit potential measurement with one or more integrated current transient measurements, with the latter used to 'calibrate' the former—i.e. use discrete measurement points from FIG. 18 to convert the continuous signal in FIG. 20 into an absolute measure of gas concentration. For example, a single current transient could be performed at the longest open circuit time, or, if for instance the ambient temperature is likely to vary significantly over the duration of the measurements then multiple current transients at different open circuit times can be used.

The information obtained from FIG. 20 can be used to deduce the rate of gas ingress into the sensor, from which the diffusional limitation of the capillary (or other barrier) can be estimated using equation 2, above. For example, one or more gradients could be taken from the curve and compared with predetermined values representative of correctly operating (or, analogously, faulty) diffusion barriers. Alternatively and/or in addition, the open circuit voltage curve can be extrapolated to long open circuit times to find $C_\infty$, which can be used for self-calibration and fault diagnosis in the same manner as described above.

In practice, any combination of the embodiments may be carried out either simultaneously or in sequence. For example, in any test cycle the processor may perform the method of the first embodiment and a method of the seventh and/or eighth embodiments to check in general whether both the electrode assembly and diffusion access are performing adequately. If either test suggests that there may be a fault, further techniques such as those of the second to sixth embodiments may be conducted. Alternatively, any single test may be performed in isolation.

The results of the tests may be logged and analysed over time to monitor any changes in the sensor's health. For example, the decreasing activity of the sensing electrode can be checked regularly using any of embodiments two to five, such that the rate of loss of activity can be deduced and the sensor replaced just before it is likely to fail.

The ability to test the sensor finds use at various stages of the sensor's lifetime. As mentioned above, the methods described could be used at the end of manufacture to check that each component of the assembled sensor is functioning as intended. In other cases, the methods may be applied to a deployed sensor in the field. This could either take place in situ (i.e. while the sensor is being used) or when the sensor is inactive (e.g. while the instrument is being recharged).

If the sensor is to be tested during a period of activity (e.g. checking a sensor that is in continuous use), the methods would include a first step of decreasing the reaction capability of the sensor (e.g. breaking the sensing circuit). The sensor would preferably be returned to its working level as soon as possible, e.g. immediately after the open circuit duration, or as soon as the necessary decay curves have been obtained. In other cases, the methods could be performed upon start-up of the instrument, in which case the step of decreasing the reaction capability is optional since the sensor may already be effectively "open circuit" during its off period. However it is preferable to establish steady state operation before beginning the open circuit period so that its duration is known. In practice, sensors are usually not left open circuit when the instrument is off, to prevent long start up times. To achieve this, the load resistor may be permanently connected, or for oxygen pump sensors the sensor circuitry may be continuously powered (e.g. via a backup battery). Another alternative is that the instrument could perform the test(s) when 'turned off' by the user, the actual process of turning off being delayed until the tests have been completed.

In summary, methods of operation electrochemical gas sensors are provided. A method of operating an electrochemical gas sensor, which electrochemical gas sensor comprises an electrode assembly disposed within a housing having a diffusion limiting barrier for gas ingress therethrough, the electrode assembly comprising a gas sensing electrode, a counter electrode, and electrolyte in communication with the gas sensing and counter electrodes, and the electrochemical gas sensor further comprising connectors for connecting the gas sensing and counter electrodes to a sensing circuit, is provided. The method in one embodiment includes:

a) exposing, for a first predetermined duration, the electrochemical gas sensor to an atmosphere containing a target gas while the gas reaction capability of the electrode assembly is substantially reduced from a working level, such that target gas is collected within the housing;

b) increasing the gas reaction capability of the electrode assembly to a level at which it consumes collected target gas and thereby outputs a signal to the sensing circuit, including an initial transient decay signal;

c) monitoring the transient decay signal; and d) analysing the rate of decay of the transient decay signal to determine whether the performance of at least one component of the electrochemical gas sensor is within acceptable limits.

The invention further provides an apparatus for operating an electrochemical gas sensor, the apparatus comprising a processor adapted for connection to an electrochemical gas sensor via a sensing circuit for control thereof, the processor being programmed to perform any of the disclosed method(s). Additionally, the invention provides a computer program product containing instructions stored in, or on, a computer readable medium, for performing any of the disclosed method(s).

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A method of operating an electrochemical gas sensor, the electrochemical gas sensor comprising an electrode assembly disposed within a housing having a diffusion limiting barrier for gas ingress therethrough, the electrode assembly comprising a gas sensing electrode, a counter electrode, and electrolyte in communication with the gas sensing and counter electrodes, and the electrochemical gas sensor further comprising connectors for connecting the gas sensing and counter electrodes to a sensing circuit, the method comprising:

a) exposing, for a first predetermined duration, the electrochemical gas sensor to an atmosphere containing a target gas while the gas reaction capability of the electrode assembly is substantially reduced from a working level, such that target gas is collected within the housing;

b) increasing the gas reaction capability of the electrode assembly to a level at which it consumes collected target gas and thereby outputs a signal to the sensing circuit, including an initial transient decay signal;

c) monitoring the transient decay signal; and d) analysing the rate of decay of the transient decay signal to determine whether the performance of at least one component of the electrochemical gas sensor is within acceptable limits, wherein, in step (b), the gas reaction capability of the electrode assembly is increased by applying a first bias potential to the gas sensing electrode, and after at least step (c) is performed, steps (a), (b) and (c) are repeated; and wherein, when step (b) is repeated, the gas reaction capability of the electrode assembly is increased by applying a second bias potential to the gas sensing electrode, the second bias potential being different to the first, to thereby determine in step (d) a variation of the transient decay signal with applied bias potential and so determine whether the reaction at the gas sensing electrode is diffusion limited or kinetically limited.

2. A method according to claim 1, wherein in step d), it is determined whether the diffusive and kinetic behaviour of the electrode assembly is within acceptable limits.

3. A method according to claim 1 wherein step (d) comprises determining a decay of the transient decay signal vs. time, to thereby obtain a combined measure of the activity of the gas sensing electrode and level of gas access to the gas sensing electrode.

4. A method according to claim 3, wherein step (d) further comprises comparing the determined rate of decay with a predetermined rate of decay to determine whether in combination the activity of the gas sensing electrode and level of gas access to the gas sensing electrode are within acceptable limits.

5. A method according to claim 1, wherein steps (a), (b) and (c) are repeated a plurality of times over a range of different potentials applied in step (b) to thereby determine in step (d) a variation of the transient decay signal with applied bias potential.

6. A method according to claim 1, wherein the applied bias voltage is controlled using a two electrode potentiostat circuit, a three electrode potentiostat circuit, or a current follower circuit.

7. A method according to claim 1 wherein in step (b), the gas reaction capability of the electrode assembly is increased by applying a bias potential to the gas sensing electrode, the bias potential varying during the decay transient signal and, in step (d), measurements from at least two portions of the decay transient signal corresponding to different applied bias potentials are taken to determine a variation of the transient decay signal with applied bias potential and so determine whether the reaction at the gas sensing electrode is diffusion limited or kinetically limited.

8. A method according to claim 1, wherein, if in step d) it is determined that the transient decay signal varies substantially with applied bias potential within a predefined bias potential range, it is concluded that the reaction at the gas sensing electrode is kinetically limited, and if in step d) it is determined that the transient decay signal substantially does not vary with applied bias potential within a predefined bias potential range, it is concluded that the reaction at the gas sensing electrode is diffusion limited.

9. A method according to claim 1, wherein, in step d), the determined variation of the transient decay signal with time is analysed to identify at what applied bias voltage a substantial change in the rate of decay of the transient decay signal is first observed to thereby obtain a measure of the activity of the gas sensing electrode.

10. A method according to claim 1 wherein the electrochemical sensor further comprises a bulk flow membrane arranged to restrict bulk flow of gas into the housing and in step d), it is determined whether the flow restriction behaviour of the bulk flow membrane is within acceptable limits, and in step d), the rate of decay of the transient decay signal is determined and compared with predetermined rates of decay indicative of bulk gas flow into the sensor in order to determine whether the flow restriction behaviour of the bulk flow membrane is within acceptable limits.

11. A method of operating an electrochemical gas sensor, the electrochemical gas sensor comprising an electrode assembly disposed within a housing having a diffusion limiting barrier for gas ingress therethrough, the electrode assembly comprising a gas sensing electrode, a counter electrode, and electrolyte in communication with the gas sensing and counter electrodes, and the electrochemical gas sensor further comprising connectors for connecting the gas sensing and counter electrodes to a sensing circuit, the method comprising:
a) exposing, for a first predetermined duration, the electrochemical gas sensor to an atmosphere containing a target gas while the gas reaction capability of the electrode assembly is substantially reduced from a working level, such that target gas is collected within the housing;
b) increasing the gas reaction capability of the electrode assembly to a level at which it consumes collected target gas and thereby outputs a signal to the sensing circuit, including an initial transient decay signal;
c) monitoring the transient decay signal;
d) repeating steps (a), (b) and (c) wherein, when step (a) is repeated, the gas sensitive electrode is exposed to the atmosphere for a second predetermined duration different from the first predetermined duration; and
e) analysing the dependency of the transient decay signal on the duration of gas collection in step (a) to determine the performance of at least one component of the electrochemical gas sensor is within acceptable limits,
wherein, in step (e), the transient decay signal for each predetermined duration is integrated over time, the result corresponding to a charge representing the gas consumed during the transient decay signal, and the variation of the charge with duration of gas collection is determined, and further comprising extrapolating the determined variation of charge with duration of gas collection to determine the level of charge where the duration of gas collection is zero, in order to determine whether the behaviour of the electrode assembly is within acceptable limits.

12. A method according to claim 11 wherein in step e) it is determined whether the diffusive behaviour of the diffusion limiting barrier is within acceptable limits.

13. A method according to claim 11 wherein steps (a), (b) and (c) are repeated a plurality of times over a range of different predetermined durations for which the gas sensitive electrode is exposed in step (a).

14. A method according to claim 11 wherein, in step (e), the transient decay signal for each predetermined duration is integrated over time, the result corresponding to a charge representing the gas consumed during the transient decay signal, and the variation of the charge with duration of gas collection is determined, from which it is determined whether the diffusive behaviour of the diffusion limiting barrier is within acceptable limits.

15. A method according to claim 14, further comprising extrapolating the determined variation to infinite gas collection duration to thereby determine a charge corresponding to collected target gas at equilibrium with the surrounding atmosphere.

16. A method according to claim 14 further comprising measuring the gradient near the origin of a plot of integrated total charge versus duration of gas collection and comparing the gradient with the steady state current of the electrochemical gas sensor to determine whether the diffusive behaviour of the diffusion limiting barrier is within acceptable limits.

* * * * *